United States Patent
Querfurth

(10) Patent No.: US 12,083,086 B2
(45) Date of Patent: Sep. 10, 2024

(54) COMPOSITIONS AND METHODS FOR TREATING ALZHEIMER'S DISEASE

(71) Applicant: ELEANORE BENNETT CHARITABLE TRUST #2, Waltham, MA (US)

(72) Inventor: Henry W. Querfurth, Wellesley, MA (US)

(73) Assignee: ELEANORE BENNETT CHARITABLE TRUST #2, Waltham, MA (US)

(*) Notice: Subject to any disclaimer, the term of this patent is extended or adjusted under 35 U.S.C. 154(b) by 0 days.

(21) Appl. No.: 17/716,156

(22) Filed: Apr. 8, 2022

(65) Prior Publication Data

US 2022/0347136 A1 Nov. 3, 2022

Related U.S. Application Data

(60) Provisional application No. 63/172,860, filed on Apr. 9, 2021.

(51) Int. Cl.
*A61K 31/192* (2006.01)
*A61K 31/405* (2006.01)
*A61P 25/28* (2006.01)

(52) U.S. Cl.
CPC .......... *A61K 31/192* (2013.01); *A61K 31/405* (2013.01); *A61P 25/28* (2018.01)

(58) Field of Classification Search
CPC .................................................. A61K 31/192
See application file for complete search history.

(56) References Cited

U.S. PATENT DOCUMENTS

| 8,912,186 | B2 | 12/2014 | Engel et al. | |
| 10,711,245 | B2* | 7/2020 | Hong | A61P 25/14 |
| 2009/0155903 | A1* | 6/2009 | Slade | C07D 403/06 |
| | | | | 435/375 |

OTHER PUBLICATIONS

CAS SciFinder, Search Results for "Allosteric activators of PDK1", Jun. 8, 2023.
CAS SciFinder, Search Results for "PS48", Jun. 8, 2023.
Engel et al., "Allosteric activation of the protein kinase PDK1 with low molecular weight compounds", The EMBO Journal, 2006, 25: 5469-5480.
Hindie et al., "Structure and allosteric effects of low-molecular-weight activators on the protein kinase PDK1", Nature Chemical Biology, Oct. 2009, 5(10): 758-764.
Mordhurst et al., "Pharmacologic Reprogramming Designed to Induce a Warburg Effect in Porcine Fetal Fibroblasts Alters Gene Expression and Quantities of Metabolites from Conditioned Media Without Increased Cell Prliferation", Cellular Reprogramming, 2018, 20(1): 38-48.
Querfurth et al., "A PDK-1 allosteric agonist neutralizes insulin signaling derangements and beta-amyloid toxicity in neuronal cells and in vitro", PLOS ONE, Jan. 21, 2022, 17(1): 1-29.
Spate et al., "PS48 can replace bovine serum albumin in pig embryo culture medium, and improve in vitro embryo development by phosphorylating AKT", Mol Reprod Dev., Apr. 2015, 82(4): 315-320.
Stroba et al., "3,5-Diphenylpent-2-enoic Acids as Allosteric Activators of the Protein Kinase PDK1: Structure-Activity Relationships and Thermodynamic Characterization of Binding as Paradigms for PIF-Binding Pocket-Targeting Compounds", Journal of Medicinal Chemistry, 2009, 52: 4683-4693.
Xu et al., "HIF-1α Regulates Glucocorticoid-Induced Osteoporosis Through PDK1/AKT/mTOR Signaling Pathway", Frontiers in Endocrinology, Jan. 28, 2020, 10(922): 1-12.

* cited by examiner

*Primary Examiner* — Paul V Ward
(74) *Attorney, Agent, or Firm* — LATHROP GPM LLP; Judith L. Stone-Hulslander; Michael J. Spellberg

(57) ABSTRACT

Provided are compositions and methods useful for sensitizing a neuron to insulin or insulin-like growth factor 1 (IGF-1), wherein the neuron is resistant to either insulin or IGF-1. Also provided are compositions and method useful for inhibiting intracellular beta amyloid peptide Aβ42-mediated decrease in neuronal viability. Also provided are compositions and methods useful for improving synaptic plasticity. Also provided are compositions and methods useful for improving learning and memory. In certain embodiments, the composition comprises (Z)-5-(4-chlorophenyl)-3-phenylpent-2-enoic acid (PS48). In certain embodiments, the method comprises contacting a neuron with PS48. In certain embodiments, the method comprises administering an effective amount of PS48 to a subject in need thereof.

11 Claims, 25 Drawing Sheets

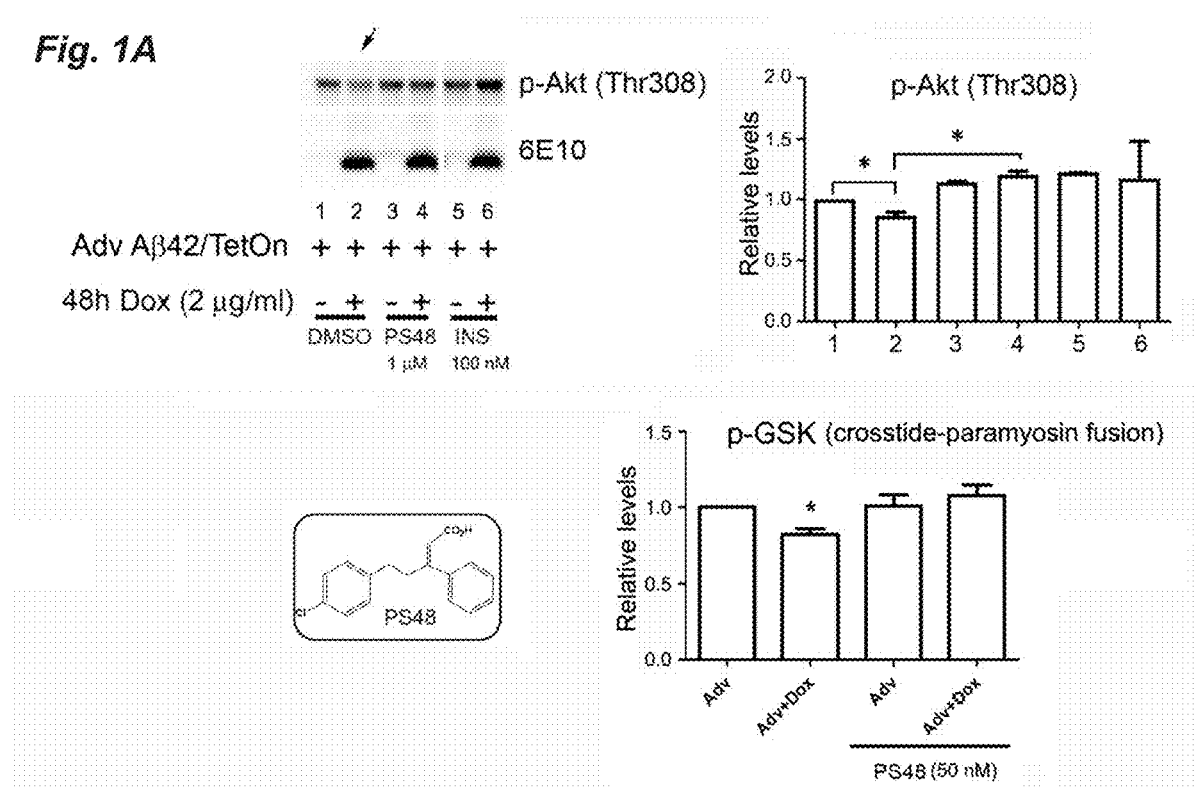
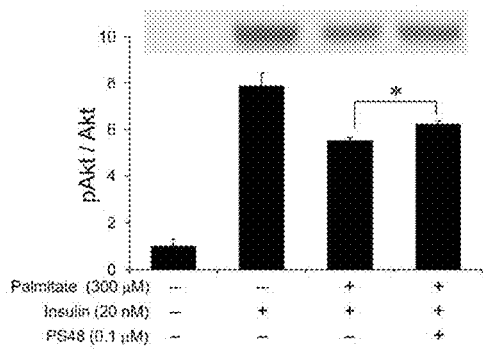
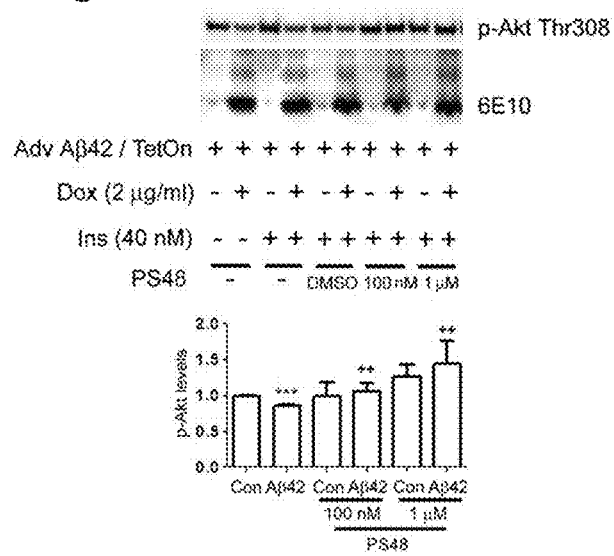

\* $p<0.05$
\*\* $p<0.01$

\*\*\* $p<0.001$
+ $p<0.05$

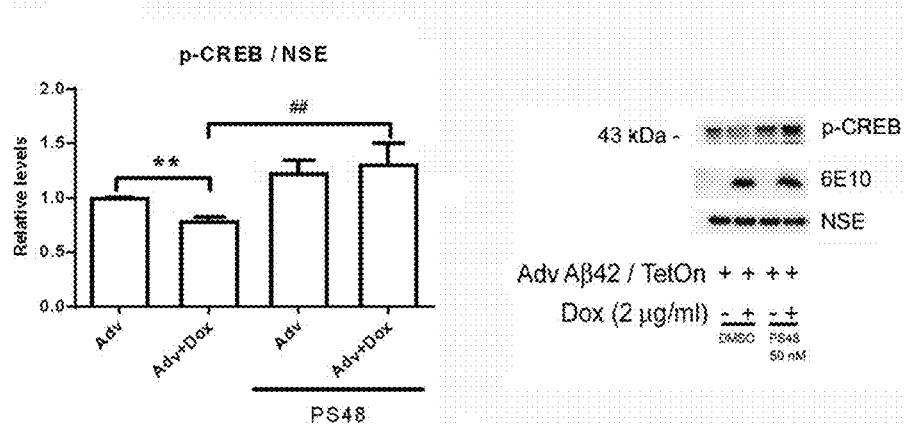

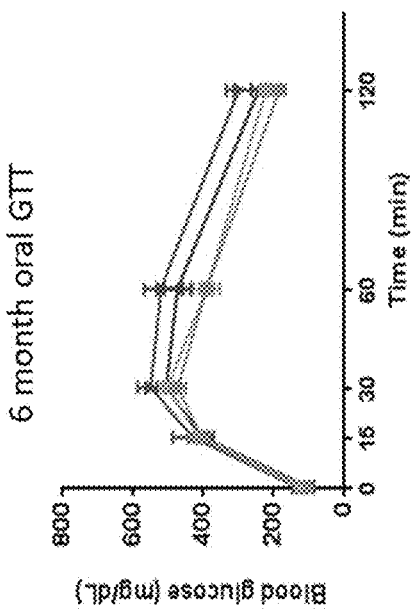
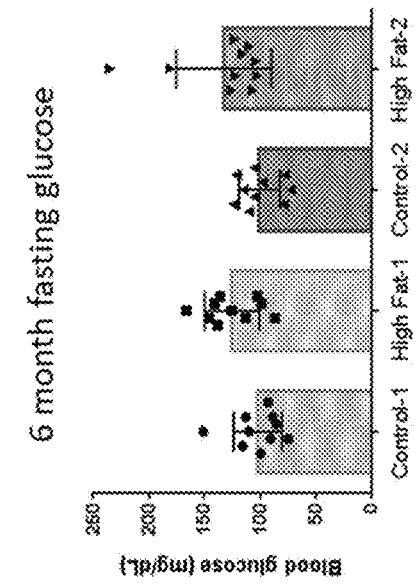
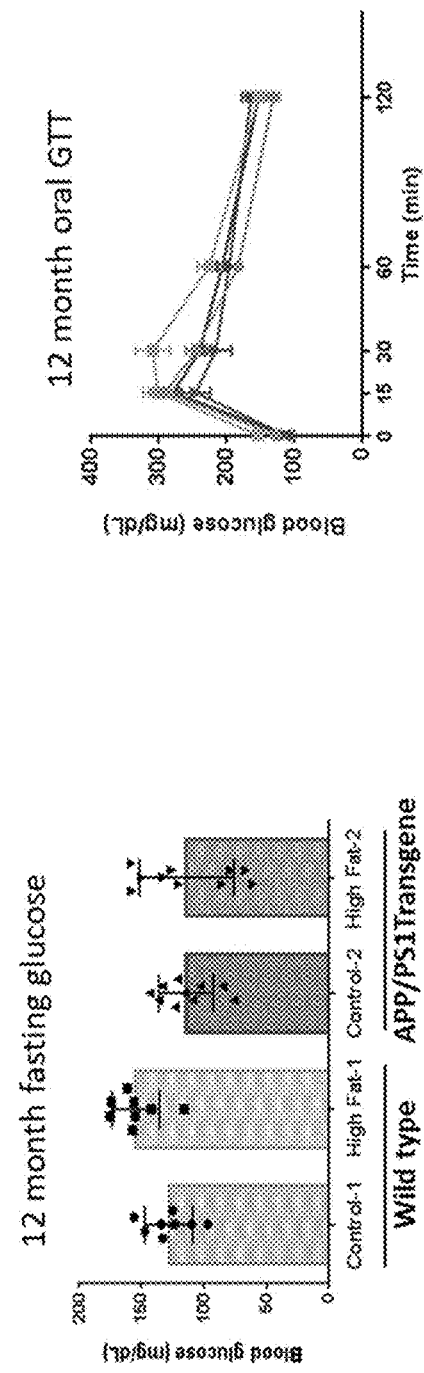
Fig. 10A
Fig. 10B
Fig. 10C
Fig. 10D

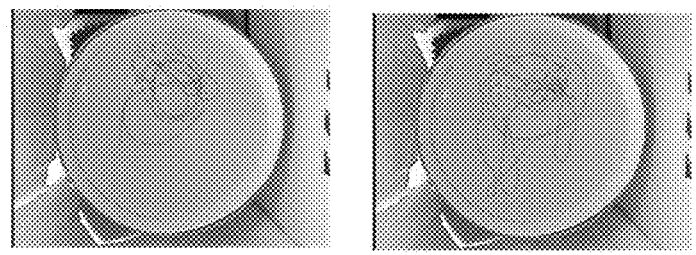
Wt (CD) no.1 and 8
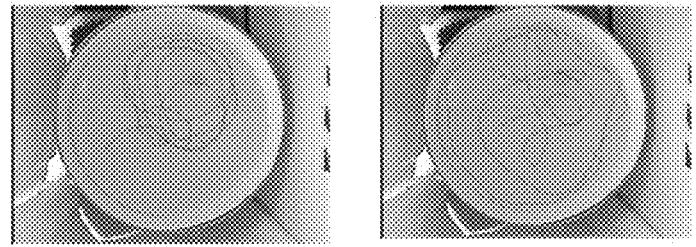
Tg (CD) no. 10 and 13
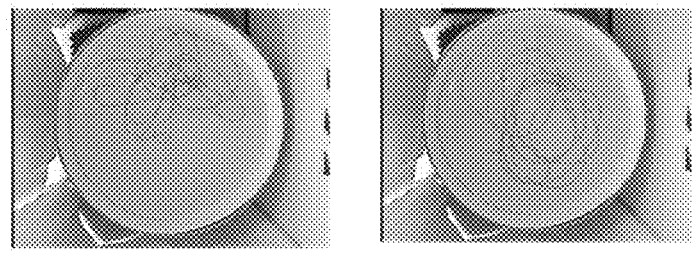
Tg (CD-PS48) no.17 and 18
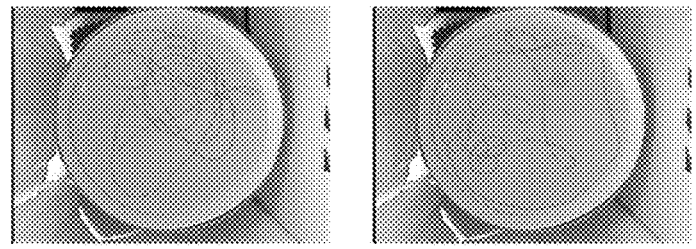
Tg (HFD) no. 27 and 28
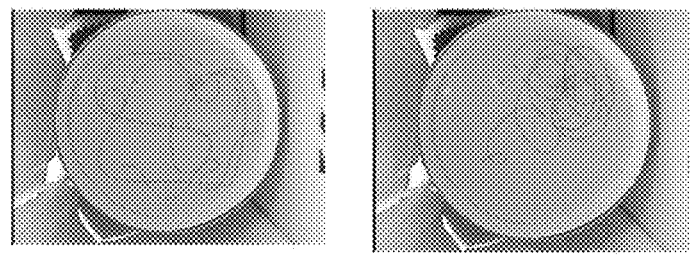
Tg (HFD) no. 37 and 40
Fig. 13A

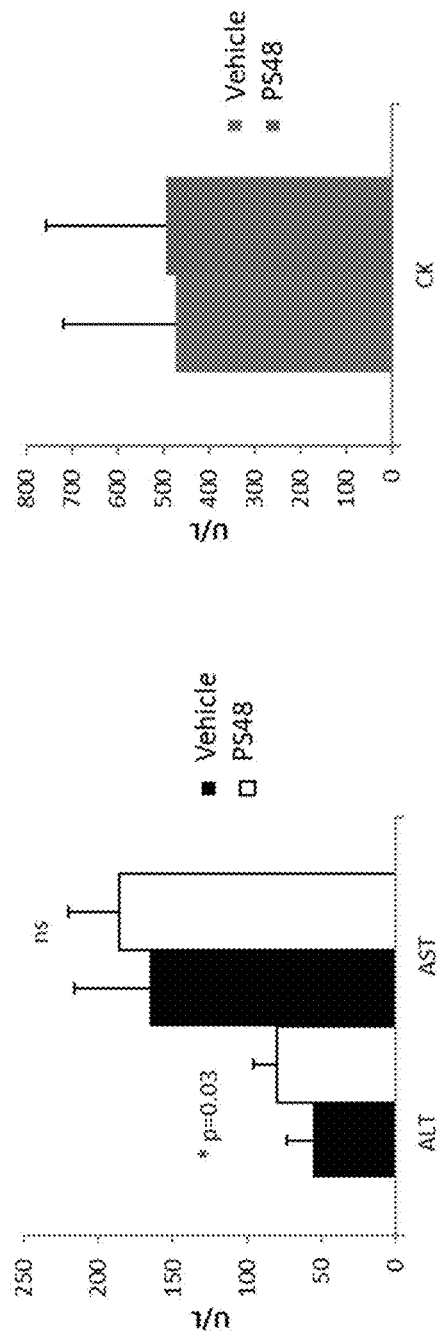
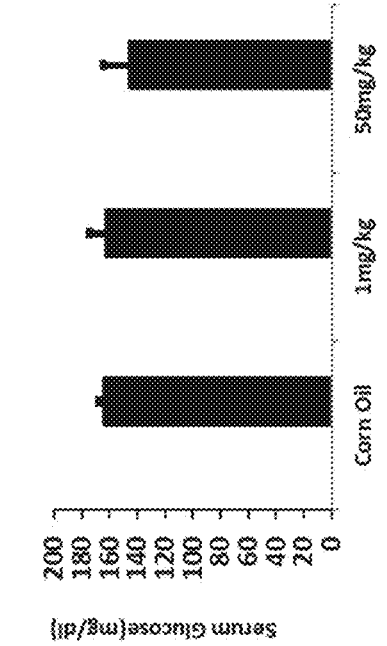
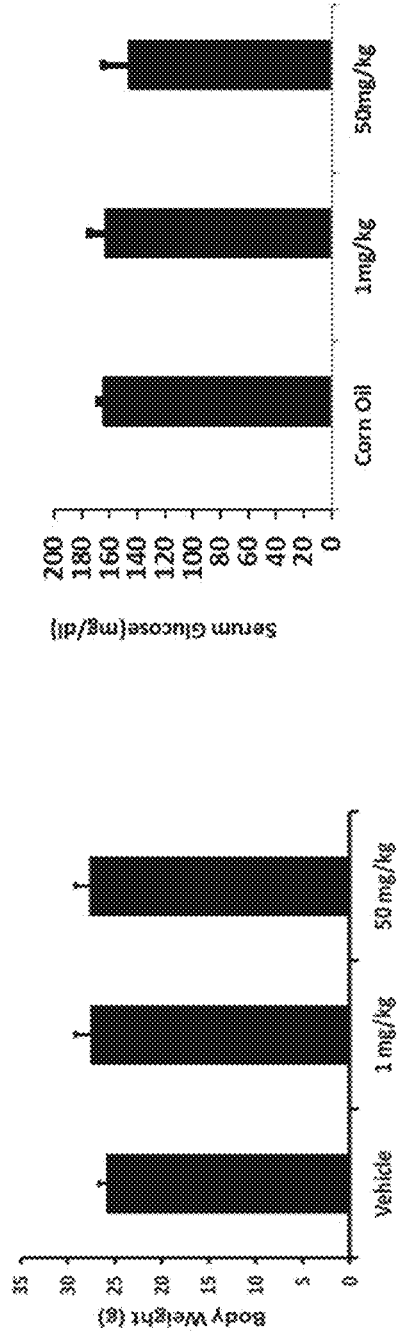
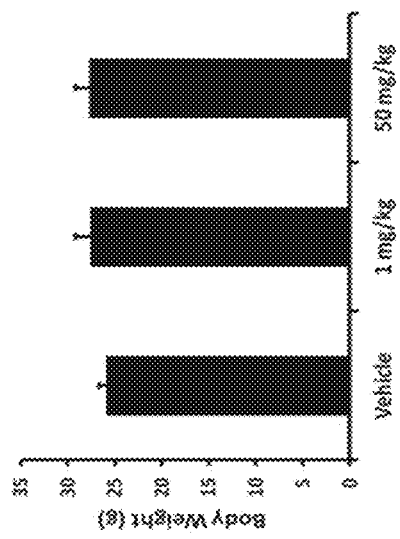
Fig. 15B
Fig. 15C
Fig. 15D
Fig. 15E

COMPOSITIONS AND METHODS FOR TREATING ALZHEIMER'S DISEASE

RELATED APPLICATION

This application claims the benefit of U.S. Provisional Patent Application Ser. No. 63/172,860 filed Apr. 9, 2021, the entire disclosure of which is hereby incorporated herein by reference.

BACKGROUND OF THE INVENTION

Alzheimer's disease (AD) is a progressive neurologic disorder that causes the brain to shrink (atrophy) and brain cells to die. It is the most common cause of dementia, a continuous decline in thinking, behavioral and social skills that affects a person's ability to function independently. Currently AD affects 5.8 million or 1 in 10 adults (10%) in the U.S.A. over age 65 and 32% in adults over age 85.

While the exact cause of AD is not known, it appears that AD is not a single entity. A common finding in patients with AD is the presence of extracellular amyloid plaque deposits in the brain. Researchers proposed that when 0-amyloid clumps together to form these deposits, it triggers neurodegenerative processes that lead to the loss of memory and cognitive ability that is observed in Alzheimer's disease.

Several phase III clinical trials of agents to prevent AD progression, based primarily on the amyloid hypothesis, have yielded disappointing overall results. These included various anti-amyloid agents such as inhibitors of γ-secretase (Semagacestat) and β-secretase (Verubecestat) and various passive immunotherapies (Bapineuzumab, Gantenerumab, Solanezumab, intravenous immunoglobulin (IVIG), Aducanumab). These realities call for targets that are not only based on the generation or removal of secreted β-amyloid (Aβ), but directly address its toxic effects on critical neuronal metabolic, plasticity, and survival signal pathways.

One less often considered offender, intra-neuronal β-amyloid peptide (Aβi) accumulation, may also be relevant to the early pathogenesis of AD. A related and potentially remediable inciting risk factor for both amyloid formation and AD progression is systemic insulin resistance (IR) and type 2 diabetes mellitus (T2DM). Moreover, there is wide recognition that the AD brain is itself an insulin-resistant end organ, a so-called type 3 diabetes condition (de la Monte et al., 2008; de la Monte et al., 2006). Type 3 diabetes occurs when neurons in the brain become unable to respond to insulin, which is essential for basic tasks, including memory and learning. Some researchers believe insulin deficiency is central to the cognitive decline of Alzheimer's disease.

Levels of insulin, insulin-like growth factor 1 (IGF-1), and their cognate receptors are significantly deregulated in AD brain. Normally, insulin and IGF-1 in brain promote energy metabolism, neuronal survival, synaptic plasticity, and memory formation. Insulin and IGF-1 receptors populate synapses where they signal through the insulin receptor substrate (IRS) and phosphatidylinositol 3-kinase/protein kinase B (PI3K/Akt) and mitogen-activated protein kinase (MAPK) pathways. The insulin-PI3K/Akt activation sequence brings together phosphoinositide-dependent protein kinase-1 (PDK-1) and Akt in a sub-membrane complex. The serine-threonine (ser/thr) kinase Akt helps maintain post-mitotic cell viability by phosphorylating pro-apoptotic mediators (forkhead box (FOXO), glycogen synthase kinase-3β (GSK-3β), and BAD proteins), thereby inactivating them. Dephosphorylation (inhibition) of Akt activates these pro-apoptotic proteins and sensitizes the cell to environmental stressors. IGF-1 and Akt together support hippocampal progenitor neurogenesis through transcription factor regulation. Insufficient insulin signaling also impacts the activity of the mechanistic target of rapamycin (mTOR), lowers levels of insulin-degrading enzyme (IDE, known to degrade Aβ), and negatively affects the translocation of GLUT-3 and -4 glucose transporter proteins in neurons. The losses of these functions to insulin resistance combine to result in neuronal energy failure, increased catabolism, inhibited synaptic plasticity, and reduced viability.

U.S. Pat. Nos. 8,969,023 and 9,618,511, the entire contents of which are incorporated herein by reference, disclose that intracellular Aβ selectively interferes with the association of PDK1 and Akt and describe non-cell-based and cell-based screening methods, respectively, to identify compounds that that protect PDK1/Akt association from intracellular Ap. U.S. Pat. Nos. 8,969,023 and 9,618,511 do not, however, disclose any such compounds identified in accordance with the methods disclosed therein.

A need still exists for effective treatment of Alzheimer's disease and related aspects of brain dysfunction, including diminishments in neuronal survival, synaptic plasticity, and learning and memory.

SUMMARY OF THE INVENTION

The instant disclosure is based, in part, on the discovery by the present inventors that select small molecules, (Z)-5-(4-chlorophenyl)-3-phenylpent-2-enoic acid, also called PS-48 or simply PS48;

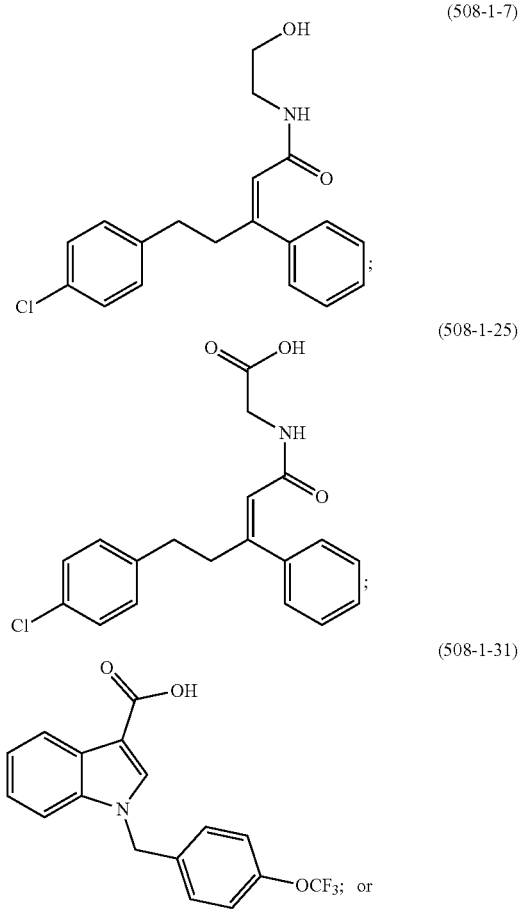

-continued (508-1-68)
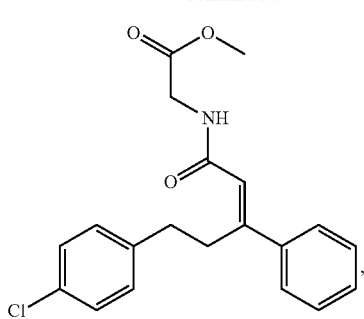

are capable of reversing several indices of insulin insensitivity (or resistance) in ex vivo and in in vitro models of AD that emphasize intracellular accumulation of β-amyloid (Aβ42). PS48, 508-1-7, 508-1-25, 508-1-31, and 508-1-68 are disclosed herein to be active at 10 nM to 1 μM in restoring normal Akt activation and in mitigating Aβ peptide toxicity.

An aspect of the present disclosure is a method of sensitizing a neuron to insulin or insulin-like growth factor 1 (IGF-1), wherein the neuron is resistant to either insulin or IGF-1, comprising contacting the neuron with an effective amount of a compound selected from the group consisting of:

(Z)-5-(4-chlorophenyl)-3-phenylpent-2-enoic acid (PS48);

(508-1-7)
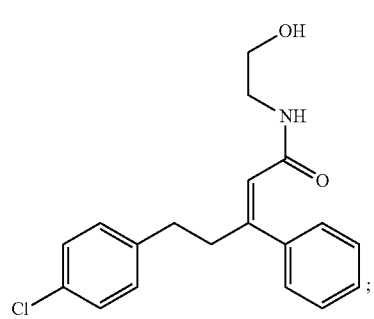

(508-1-25)
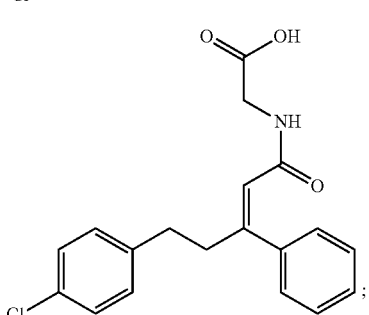

(508-1-31)
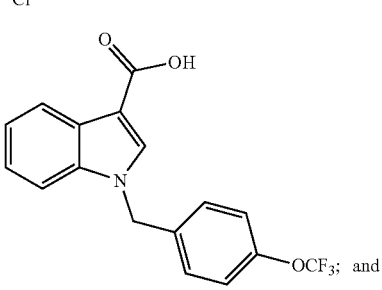

-continued (508-1-68)
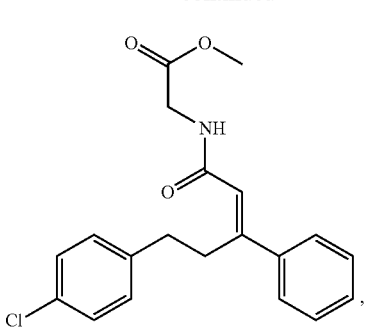

thereby restoring insulin pathway regulation toward normal.

In certain embodiments, the neuron comprises intracellular beta amyloid peptide Aβ42 or another endogenous neurotoxin that similarly compromises protein kinase B (Akt) signaling pathway, producing a cellular pre-diabetic-like or Alzheimer's disease pathological state in the neuron.

In certain embodiments, the endogenous neurotoxin is selected from the group consisting of palmitic acid and ceramide.

In certain embodiments, the effective amount is 10 nM to 100 μM.

In certain embodiments, the effective amount is at least 100 nM.

In certain embodiments, the sensitizing occurs without overstimulation of phosphatidylinositide-3-kinase (PI3K)/protein kinase B (Akt) signaling.

In certain embodiments, the contacting occurs in vivo.

In certain embodiments, the contacting occurs ex vivo.

An aspect of the present disclosure is a method of inhibiting intracellular beta amyloid peptide Aβ42- or other endogenous neurotoxin-mediated decrease in neuronal viability (or survival), comprising contacting a neuron comprising intracellular beta amyloid peptide Aβ42 or another endogenous neurotoxin that similarly compromises protein kinase B (Akt) signaling pathway with an effective amount of a compound selected from the group consisting of:

(Z)-5-(4-chlorophenyl)-3-phenylpent-2-enoic acid (PS48);

(508-1-7)
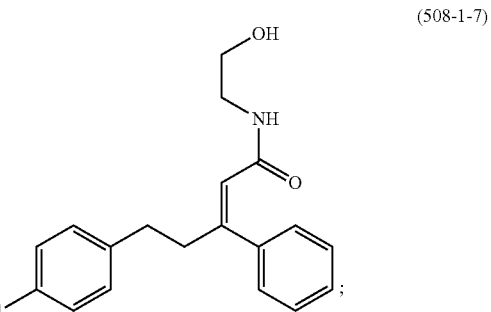

-continued

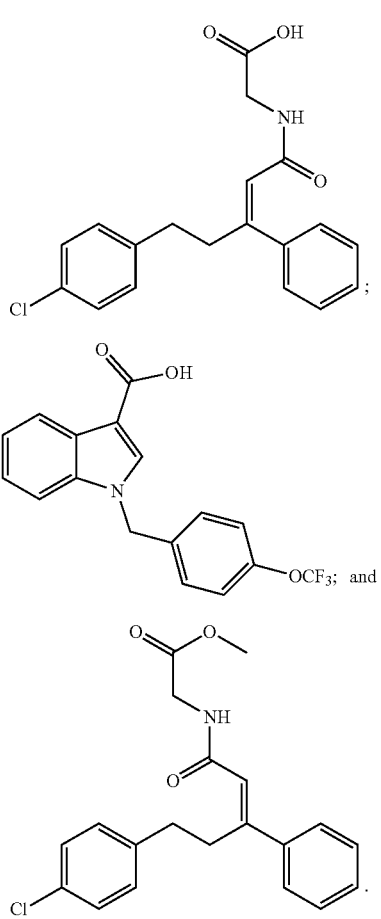

(508-1-25)

(508-1-31)

(508-1-68)

In certain embodiments, the other endogenous neurotoxin is selected from the group consisting of palmitic acid and ceramide.

In certain embodiments, the effective amount is 10 nM to 100 μM.

In certain embodiments, the effective amount is at least 10 μM.

In certain embodiments, the contacting occurs in vivo.

In certain embodiments, the contacting occurs ex vivo.

An aspect of the present disclosure is a method of improving synaptic plasticity, an activity-dependent lasting change in synaptic strength, comprising contacting a neuronal tissue with an effective amount of a compound selected from the group consisting of:

(Z)-5-(4-chlorophenyl)-3-phenylpent-2-enoic acid (PS48);

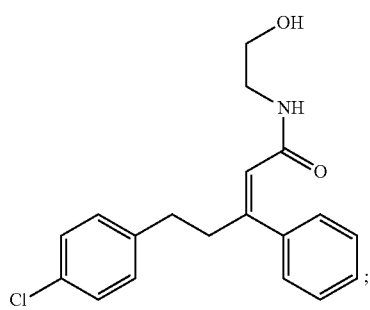

(508-1-7)

-continued

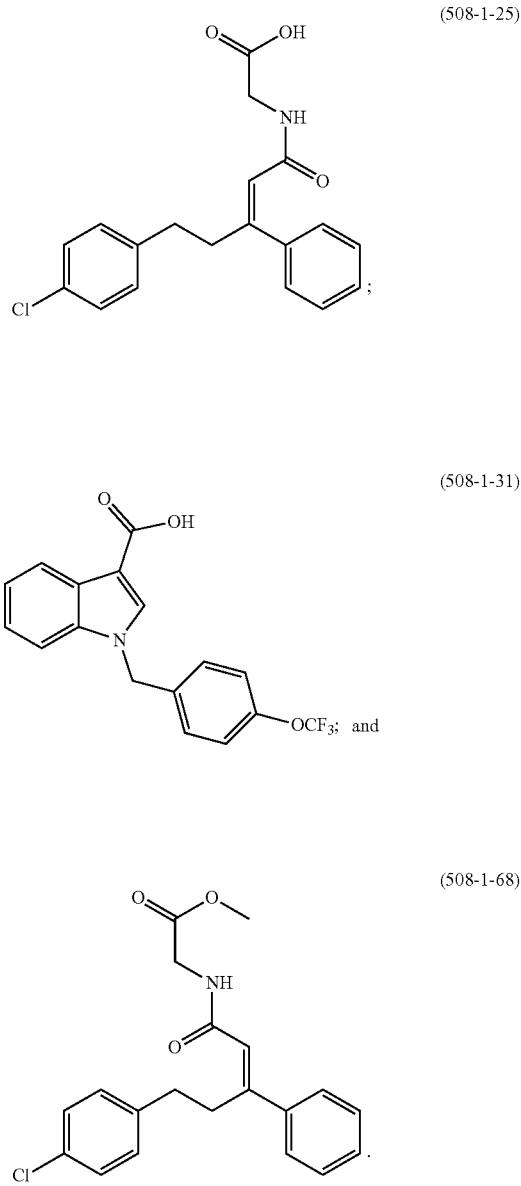

(508-1-25)

(508-1-31)

(508-1-68)

In certain embodiments, the neuronal tissue comprises intraneuronal beta amyloid peptide Aβ42.

In certain embodiments, the neuronal tissue is contacted with amyloid peptide Aβ42.

In certain embodiments, the effective amount is 10 nM to 10 μM.

In certain embodiments, the effective amount is at least 100 nM.

In certain embodiments, the contacting occurs in vivo.

In certain embodiments, the contacting occurs ex vivo.

An aspect of the present disclosure is a method of improving learning and memory, in rodents and other mammals, comprising administering to a subject in need thereof an effective amount of a compound selected from the group consisting of:

(Z)-5-(4-chlorophenyl)-3-phenylpent-2-enoic acid (PS48);

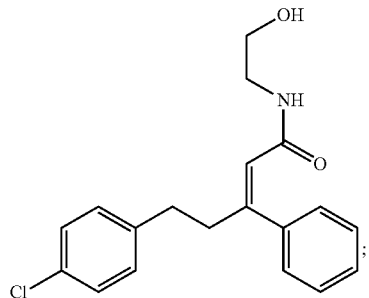
(508-1-7)

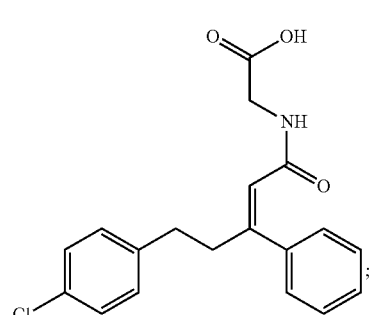
(508-1-25)

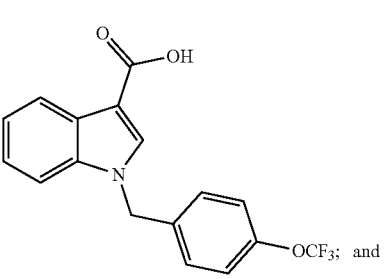
(508-1-31)

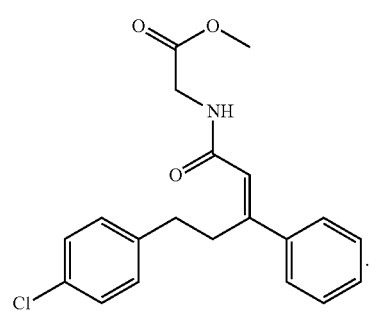
(508-1-68)

In certain embodiments, the subject has intraneuronal beta amyloid peptide Aβ42.

In certain embodiments, the effective amount is about 1 mg/kg/day to about 50 mg/kg/day.

In certain embodiments, the effective amount is at least about 10 mg/kg/day.

In certain embodiments, the administering is orally administering.

In certain embodiments, the administering is parenterally administering.

In one aspect, the disclosure provides a compound comprising or consisting of

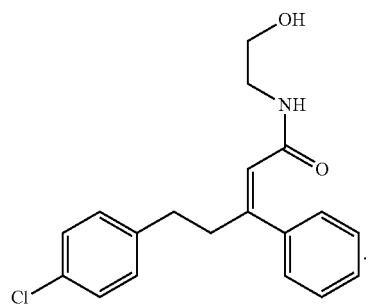
(508-1-7)

In one aspect, the disclosure provides a compound comprising or consisting of

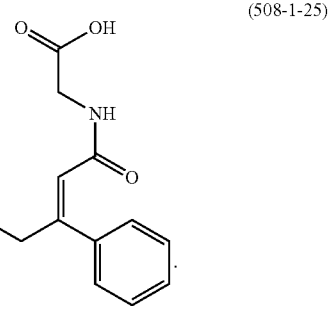
(508-1-25)

In one aspect, the disclosure provides a compound comprising or consisting of

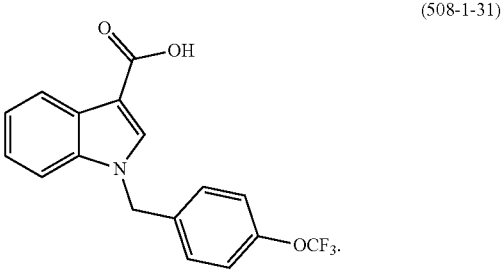 [SMILES: O=C(O)c1cn(Cc2ccc(OC(F)(F)F)cc2)c2ccccc12]
(508-1-31)

In one aspect, the disclosure provides a compound comprising or consisting of

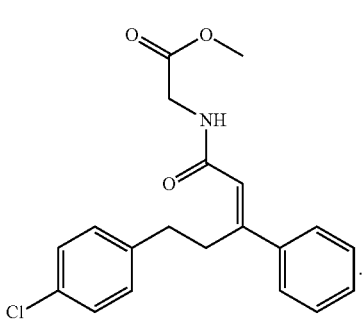
(508-1-68)

BRIEF DESCRIPTION OF THE DRAWINGS

FIG. 1A. PS48 or insulin restored Akt activation in β-amyloid-expressing cells. FIG. 1A, left: SH-SY5Y cultures were infected with Adenovirus encoding Aβ42 (Adv; 24-36 hrs) and induced with Doxycycline (Dox; 46 additional hrs). Amyloid-bearing cells showed inhibited Akt phosphorylation (lane 2 arrow). PS48 (1 µM) or high dose insulin (INS; 100 nM) added 2 hrs before doxycycline induction (as pre-treatment) restored basal Akt activation levels (lane 4 and 6). Insulin 40 nM was added to all cultures 20 min prior to harvest. PS48 alone did not over-stimulate basal Akt (lane 3 vs 1). 6E10, anti-Aβ42. FIG. 1A, right: Quantification of the restoration of inhibited Akt activation by PS48. pT308 Akt levels were measured densitometrically (normalized relative fluorescence units (RFU)). n=3 experiments. Error bars are 1SE relative to lane 1 (control); * p<0.05. FIG. 1A, lower panel: in vivo-in vitro coupled assay of Akt activity. Akt was immunoprecipitated from SH-SY5Y cells that were infected with Adenovirus and treated with doxycycline to induce Aβ42 expression. Insulin was added 20 min before harvest. Phosphorylation of a 27 kDa GSK3a/P consensus peptide substrate (crosstide-paramyosin fusion, 250 ng) proceeded in vitro after adding 200 µM ATP to the immunoprecipitate. PS48 pre-treatment (50 nM) added to the cells 2 hrs before doxycycline addition prevented the inhibition of peptide phosphorylation by Aβ42, confirming the p-Akt experiments. (Western not shown, n=3; * p<0.05). PS48 structure is shown at left.

FIG. 1B. Non-amyloid-based insulin resistance model. Partial restoration of insulin-induced Akt activation in rat primary cortical neurons exposed to the fatty acid neurotoxin palmitate (300 µM). PS48 (100 nM, 24 hrs) partly reversed inhibition of Akt Ser473 phosphorylation by palmitate in insulin-stimulated cells (20 nM, 15 mins before lysis). The same result was obtained in ceramide-treated (50 µM) primary neurons (not shown); * p<0.05. Representative western blot above, n=3 experiments.

FIG. 1C. SH-SY5Y neuronal (Western shown) and C2C12 myotube cells (data combined for the quantification in bar graph) expressed Aβ42 after doxycycline induction. Aβ42 expression (detection with 6E10) significantly inhibited the insulin-stimulated phosphorylation (activation) of Akt (lanes 4 vs 3, bar 2 vs bar 1). PS48 was added 2 hrs ahead of doxycycline and cells harvested in 24 hours. Insulin was added to all cultures last 30 min before harvest. PS48 100 nM and 1 µM (and 10 µM not shown) each significantly reversed the Aβ42 effect, lanes 8 and 10 vs 4; bar 4 and 6 vs bar 2. *** p<0.005 vs vehicle control (Con), ++ p<0.01 compared to Aβ42 (bar 2). DMSO was vehicle control (n=3).

FIG. 8A. Results of Aβ42-expression and PS48 on endogenous phospho-levels of Akt-effector proteins CREB, GSK3α/β, and mTOR. Doxycycline-induced Aβ42 expression reduced p-CREB levels in SH-SY5Y cells. PS48 (50 nM) mitigated the Aβ42 effect. Whole cell extracts were fractionated by Western and probed with monoclonal anti-pCREB pS133. The signals corresponding to endogenous p-CREB levels were quantified and normalized to neuron specific enolase (NSE) (bar graph on left). n=3 experiments. **$p<0.01$, ##$p<0.01$. All cells were stimulated with insulin 250 ng/ml for 30 min before harvest.

FIG. 8B. PS48 over time (1 μM; 0 to 2 hours) and concentration (20 min; 0-100M) was applied to SH-SY5Y cells. No changes in cellular phospho-GSK levels were observed.

FIG. 8C. Bottom. Downstream mTOR substrate phosphorylation was unchanged by Aβ42 expression or PS48 treatment (1 or 10 μM) for 2-4 hrs before doxycycline addition.

FIG. 10A. Fasting glucose for different groups of mice at 6 months of age, no PS48. Control-1 and High Fat-1, wild-type; Control-2 and High Fat-2, transgene.

FIG. 10B. Oral glucose tolerance test for different groups of mice at 6 months of age, no PS48.

FIG. 10C. Fasting glucose for different groups of mice at 12 months of age, no PS48.

FIG. 10D. Oral glucose tolerance test for different groups of mice at 12 months of age, no PS48.

FIG. 13A. Probe phase of Morris Water Maze. Memory acquisition for the location of the escape platform location is tested in 12-month-old APP/PS1 transgenic and littermate mice. The removed escape platform was located in the northeast quadrant of the tank. Track records are shown for 2 representative animals from each group. The 10 cm platform is indicated by the shaded circle in the upper right quadrant. CD, control diet; HFD, high fat diet; Tg, transgenic; Wt, wild-type.

FIG. 15B. Alanine transaminase (ALT) and aspartate transaminase (AST) in mice treated daily for 14 days with PS48 or vehicle administered intravenously. Data are mean±SEM. n=6 for each group.

FIG. 15C. Muscle creatine kinase (CK) in mice treated daily for 14 days with PS48 or vehicle administered intravenously. Data are mean±SEM. n=6 for each group.

FIG. 15D. Average body weight on PS48 (1 mg/kg or 50 mg/kg) or vehicle administered daily for 14 days by oral gavage. Data are mean±SEM. n=6 for each group.

FIG. 15E. Fasting serum glucose after 14 days administration by oral gavage of PS48 (1 mg/kg or 50 mg/kg) or vehicle. Data are mean±SEM. n=6 for each group.

DETAILED DESCRIPTION OF THE INVENTION

Figure 2A:
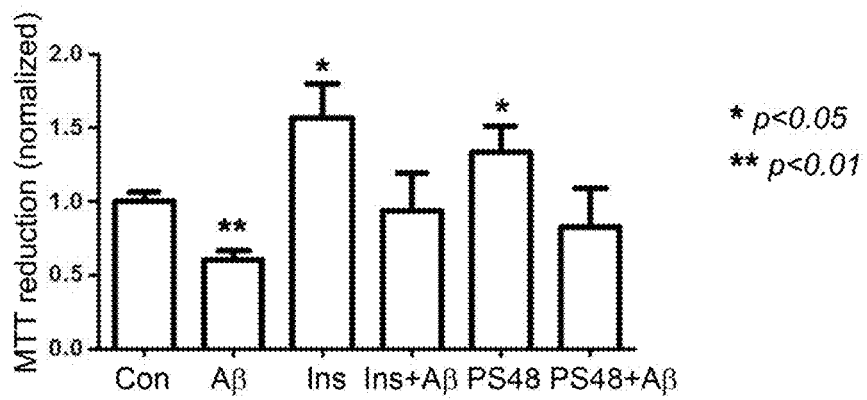
FIG. 2A. Cell viability as measured by MTT assay. SH-SY5Y cells were exposed to Adv TRE-Aβ±doxycycline to induce Aβ42, then harvested at 48 hrs. Amyloid-bearing cells were less viable compared to control (Con; bar 2 vs control bar 1; ** p<0.01). Pretreatment of cultures (before doxycycline) with high dose insulin (100 nM) or PS48 (10 µM) reverted cells to basal condition or better (bars 4 and 6 vs control, * p<0.05). The same cytoprotection was obtained in C2C12 myotubes.

The consequence of excess Aβ42 accumulation in producing neuronal insulin resistance and accompanying changes to the PI3K/Akt axis has been studied. It has been reported that the inhibitory effect of Aβ42 oligomers on hippocampal long-term potentiation (LTP) is through several insulin-sensitive pathways, including PI3K/Akt, and is reversed by insulin (De Felice et al., 2009; Townsend et al., 2007). One reported mechanism is the caspase-mediated cleavage of Akt1 (Jo et al., 2011). Extracellular, soluble or oligomeric Aβ also has been reported to inhibit the binding of insulin to insulin receptors (IR) in neurons (Xie et al., 2002), resulting in downregulation (removal) of IR from the membrane (De Felice et al., 2009; Zhao et al., 2008). Aβ oligomers have further been shown to inhibit insulin-induced phosphorylation of both the IR (Zhao et al., 2008) and Akt (Townsend et al., 2007).

The resistance to insulin/IGF action that characterizes AD brain has also been linked to the inhibitory feedback phosphorylation of IRS-1 (S616 and S636) by pS6K (O'Neill et al., 2012; Talbot et al., 2012a). Aβ has been implicated in this phenomenon too by directly activating mTOR (and indirectly, mTOR target, pS6K) in studies using transgenic models (Caccamo et al., 2010; Caccamo et al., 2011; Majumder et al., 2012). Aβ enables the phosphorylation of PRAS40, an inhibitory subunit of the mTOR complex, thereby de-repressing mTOR activity (Caccamo et al., 2011). The end result is a decrease in IRS-1 levels (Kapogiannis et al., 2015; O'Neill et al., 2012). The inflammatory cytokine TNFα also mediates the same outcome (Lourenco el al., 2013; Rui el al., 2001).

PI3K/PDK/Akt signaling in AD has been reported to be abnormally stimulated (Griffin et al., 2005; Moloney et al., 2010; Pei et al., 2003; Pietri et al., 2013; Rickle et al., 2004; Talbot et al., 2012b). Accordingly, over-activation of downstream mTORC1 has been reported (Colin et al., 2005; Emamian et al., 2004; Lee et al., 2009; Liu et al., 2011; Steen et al., 2005), resulting in loss of autophagy markers (Perluigi et al., 2014; Tramutola et al., 2015). The mechanisms underlying the somewhat paradoxical hyperactivity of Akt and mTOR under basal (unstimulated) conditions, are not clearly understood. Experimental intra-hippocampal anti-Aβ antibody injections or anti-Aβ immunization normalized the abnormal activation of Akt and mTOR in transgenic AD mice (Caccamo et al., 2011; Chiang et al., 2018).

It has been suggested that A3 directly inactivates phosphatase and tensin homolog (PTEN) and thereby disinhibits PI3K (Bhaskar et al., 2009; Tramutola et al., 2015). PTEN negatively regulates PI3K/Akt/mTOR by removing a phosphate from the lipid signaling molecule phosphatidylinositol 3,4,5-trisphosphate (PIP3). One seminal study found all insulin receptor substrate 1(IRS-1)-S and -Y sites were hyperphosphorylated in live AD hippocampal and cerebellar tissue, essentially isolating IRS-1 from binding to IR and to p85-PI3K. The likely cause was the intrinsic over-activation of mTOR/S6K as well as other ERK, JNK, IKKB and Akt kinases. Nevertheless, the same study importantly demonstrated that there was resistance to insulin and IGF-1 action (at 1 or 10 nM) (i.e., a 90% decrease in pAkt, pIRS-1, pIR, and pmTOR activations in response to insulin stimulation relative to normal brain tissue) (Talbot et al., 2012a).

In contrast, there is also opposing evidence that altered insulin signaling is associated with the deactivation of basal Akt in various AD models, a configuration also consistent with a state of insulin resistance in AD. Moreover, the same is noted in post mortem tissue from other neurodegenerative diseases such as Huntington's and Parkinson's diseases (Colin et al., 2005; Guttuso et al., 2019; Humbert et al., 2002; Sekar & Taghibiglou, 2018). For instance, in both transgenic (2×APP/PS1) and in vitro viral-mediated AD models, inhibition of PTEN instead rescued synaptic and cognitive impairments and was mediated by the stimulation of PI3K/Akt (Knafo et al., 2016). Conversely, PTEN overexpression led to synaptic depression (decreased LTP, augmented long-term depression (LTD)). Aβ peptides applied to hippocampal neurons induced the same synaptic defects and dephosphorylation of Akt by recruiting PTEN to dendritic spines where it becomes overactivated (Knafo et al., 2016). In a study of transgenic Tg2576 mice, where cellular Aβ is co-localized to mTOR, PTEN was found to have an inhibitory role (Ma et al., 2010). In another example, a reduction in mTOR signaling and basal phospho-Akt marker levels, as well as enzymatic activities, was described in synaptosomes from 2×APP/PS1 mice and in post-mortem AD brain. This was correlated with inhibited brain-derived neurotrophic factor (BDNF)-stimulated protein translation, and oxidatively damaged synaptic Akt was held responsible. Akt enhancement rescued protein translation (Ahmad et al., 2017). Similar evidence for deactivation of Akt comes from experiments using growth factor stimulation in rat primary cortical neurons (PCNs) and N2a cells, where oligomeric Aβ treatment inhibited BDNF-induced Akt/mTOR signal activation (Chen et al., 2009; Jimenez et al., 2011).

Due to conflicting reports and the paucity of preclinical and clinical data on direct Akt/PDK-1 intervention in AD models, we set out to test the hypothesis that targeting insulin resistance at this step may be beneficial. In a previous study, we showed that intraneuronal Aβ42 (Aβi) expression led to a decrease in the levels of phosphoAkt and activity, causing pTau accumulation and apoptosis (Magrane et al., 2005). Aβi specifically inhibited association of PDK-1 with Akt, resulting in the loss of normal insulin-stimulated pathway activation (Lee et al., 2009; Suhara et al., 2003). This mechanism presents a novel drug discovery target for the treatment of AD. We reasoned that an allosteric ligand acting on the Akt/PDK-1/mTORC2 interaction complex could normalize insulin sensitivity and restore the imbalance in Akt activity. Promising results from clinical trials of insulin sensitizers (metformin), liraglutide and exendin-4 (GLP-1 agonists) (Batista et al., 2018; Bomfim et al., 2012) and intranasal (IN) insulin further supported efforts to find new targets in this pathway (Craft et al., 2012; McClean et al., 2011; Reger et al., 2006; Risner et al., 2006; Watson et al., 2005). Moreover, the approach to reestablish insulin sensitivity in AD need not be dependent on the amyloid hypothesis to be relevant.

The instant disclosure presents preclinical findings using PS48, a chlorophenyl pentenoic acid and allosteric activator of PDK-1. The findings disclosed herein demonstrate, for the first time, that PS48 is capable of sensitizing a neuron to insulin or insulin-like growth factor 1 (IGF-1), wherein the neuron is resistant to either insulin or IGF-1, thereby restoring insulin pathway regulation toward normal.

The findings disclosed herein further demonstrate, for the first time, that PS48 is capable of inhibiting intracellular beta amyloid peptide Aβ42- or other endogenous neurotoxin-mediated decrease in neuronal viability.

The findings disclosed herein further demonstrate, for the first time, that PS48 is capable of improving synaptic plasticity.

The findings disclosed herein further demonstrate, for the first time, that PS48 is capable of improving learning and memory.

As used herein, "PS48" refers to (Z)-5-(4-chlorophenyl)-3-phenylpent-2-enoic acid, the structure of which is represented below:

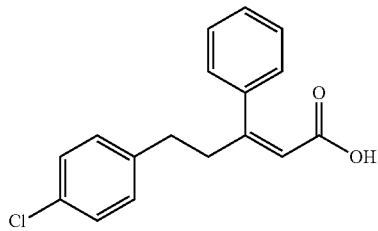 [SMILES: O=C(O)/C=C(/CCc1ccc(Cl)cc1)c1ccccc1]

PS48 is available from a number of commercial suppliers. PS48 has been shown to be a PKB Kinase (phosphoinositide-dependent protein kinase-1, PDK1) activator (Kd=10.3 μM). Studies have indicated that this compound selectively binds to the PIF-binding pocket of PKB Kinase (PDK1). This is a distinct region separate from the ATP binding site of PDK1.

As used herein, "PS47" refers to the corresponding E-isomer of PS48. PS47 is also available from a number of commercial suppliers and is known to be inactive with respect to PDK1. The molecular weight of PS47, like that of PS48, is 286.8 g/mol.

As used herein, "Aβ42" refers to a 42-amino acid residue form of amyloid β. Aggregation of amyloid 0 (A3) plays a key role in the pathogenesis of Alzheimer's disease (AD). Aβ is a proteolytic product of amyloid precursor protein (APP) by β- and γ-secretases. The variable cleavage by γ-secretase at the C-terminus of Aβ sequence results in two major Aβ isoforms: Aβ42 (42 residues long) and Aβ40 (40 residues long). The only primary structural difference between Aβ42 and Aβ40 is the two additional C-terminal residues on Aβ42. Aβ42 is the major component of amyloid plaques in AD brains, while Aβ40 is detected only in a subset of plaques and vessel walls. The amino acid sequence of Aβ42 is DAEFRHDSGYEVHHQKLVFFAEDVGSNK-GAIIGLMVGGVVIA (SEQ ID NO: 1). Aβ42 is more prone to oligomerization and is much more pathogenic or toxic than is Aβ40.

An aspect of the invention is a method of sensitizing a neuron to insulin or insulin-like growth factor 1 (IGF-1), wherein the neuron is resistant to either insulin or IGF-1. The method comprises contacting the neuron with an effective amount of (Z)-5-(4-chlorophenyl)-3-phenylpent-2-enoic acid (PS48), thereby restoring insulin pathway regulation toward normal. In certain embodiments, restoration toward normal includes reducing resistance to insulin. In certain embodiments, restoration toward normal includes reducing resistance to IGF-1. In certain embodiments, insulin pathway regulation is fully restored to normal.

In certain embodiments, the neuron comprises intracellular beta amyloid peptide Aβ42 or another endogenous neurotoxin that similarly compromises the protein kinase B (Akt) signaling pathway, producing a cellular pre-diabetic-like or Alzheimer's disease pathological state in the neuron. Aβ42 acts like a sort of endogenous neurotoxin by inducing apoptosis. Other endogenous neurotoxins include, without limitation, palmitic acid and ceramide. Palmitic acid induces apoptosis by increasing oxidative stress in neurons. Ceramide causes apoptosis by modulating phosphorylation states of proteins, including those that regulate insulin signaling, activating enzymes such as interleukin-1β converting enzyme (ICE)-like proteases, which promote apoptosis, or inhibiting Akt phosphorylation and kinase activity through activation of protein phosphatase 2A.

In certain embodiments, the effective amount of PS48 is 10 nM to 100 μM. These concentrations may be as measured within the neuron or in the environment surrounding the neuron. In various embodiments, the effective amount of PS48 can be about 10 nM to about 100 nM, about 100 nM to about 500 nM, about 500 nM to about 750 nM, about 750 nM to about 1000 nM, about 1 μM to about 10 μM, about 10 μM to about 50 μM, about 50 μM to about 75 μM, or about 75 μM to about 100 μM. In various embodiments, the effective amount of PS48 can be 10 nM to 100 nM, 100 nM to 500 nM, 500 nM to 750 nM, 750 nM to 1000 nM, 1 μM to 10 μM, 10 μM to 50 μM, 50 μM to 75 μM, or 75 μM to 100 μM. Certain exemplary effective amounts of PS48 include about 10, about 20, about 30, about 40, about 50, about 60, about 70, about 80, about 90, about 100, about 120, about 140, about 160, about 180, about 200, about 250, about 300, about 350, about 400, about 450, about 500, about 550, about 600, about 650, about 700, about 750, about 800, about 850, about 900, about 950, or about 1000 nM, as well as about 10, about 20, about 30, about 40, about 50, about 60, about 70, about 80, about 90, or about 100 μM. Certain exemplary effective amounts of PS48 include 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, or 1000 nM, as well as 10, 20, 30, 40, 50, 60, 70, 80, 90, or 100 μM.

As used herein, the term "about" connotes a stated value plus or minus 10 percent of said value. Thus for example the phrase "about 100 nM" encompasses 90 nM to 110 nM, including every value therebetween.

In certain embodiments, the effective amount is at least 100 nM. For example, the effective amount of PS48 can be 100, 120, 140, 160, 180, 200, 250, 300, 350, 400, 450, 500, 550, 600, 650, 700, 750, 800, 850, 900, 950, or 1000 nM, as well as 10, 20, 30, 40, 50, 60, 70, 80, 90, or 100 μM.

Notably, in certain embodiments, the sensitizing occurs without overstimulation of phosphatidylinositide-3-kinase (PI3K)/protein kinase B (Akt) signaling.

In certain embodiments, the contacting occurs in vivo. For example, in such an embodiment, PS48 is administered to a subject, preferably a subject in need thereof. As used herein, a "subject" refers to a mammal. In certain embodiments, a subject is a mouse, rat, guinea pig, rabbit, cat, dog, goat, sheep, pig, horse, or cow. In certain embodiments, a subject is a non-human primate. In some embodiments, a subject is a human.

In certain embodiments, the contacting occurs ex vivo. For example, in certain embodiments, PS48 is contacted with a slice or slab of live brain tissue. Typically, freshly prepared brain tissue is immersed in suitable culture medium and maintained at physiological conditions of temperature and oxygen. For example, a suitable medium could be oxygenated (95% $O_2$/5% $CO_2$) artificial cerebrospinal fluid (ACSF) containing: 126 mM NaCl, 3 mM KCl, 1.25 mM $NaH_2PO_4$, 1 mM $MgSO_4$, 2 mM $CaCl_2$, 26 mM $NaHCO_3$, 10 mM dextrose. The PS48 (or control agent) can be present in or added to the culture medium in an amount suitable to achieve the desired amount or concentration of PS48 (or control agent). In certain embodiments, the brain tissue can be in the form of an organoid.

In certain embodiments, the contacting occurs in vitro. For example, in certain embodiments, the PS48 is contacted with neural cells such as primary culture cells or neural cell line cells, e.g., SH-SY5Y and N2a cell lines (ATCC, Manassas, VA; Sigma, St. Louis, MO). Typically, the cells are immersed in suitable culture medium and maintained at physiological conditions of temperature and oxygen. The PS48 (or control agent) can be present in or added to the culture medium in an amount suitable to achieve the desired amount or concentration of PS48 (or control agent).

In certain embodiments, the cells in vitro or the brain tissue ex vivo can be in the form of a brain organoid. For a review of brain organoids, see Sidhaye and Knoblich, *Cell Death Differ* 28: 52-67 (2021).

An aspect of the invention is method of inhibiting intracellular beta amyloid peptide Aβ42- or other endogenous neurotoxin-mediated decrease in neuronal viability. The method comprises contacting a neuron comprising intracellular beta amyloid peptide Aβ42 or another endogenous neurotoxin that similarly compromises protein kinase B (Akt) signaling pathway with an effective amount of (Z)-5-(4-chlorophenyl)-3-phenylpent-2-enoic acid (PS48).

In accordance with this aspect of the invention, the neuron comprising intracellular beta amyloid peptide Aβ42 or another endogenous neurotoxin that similarly compromises Akt signaling pathway, the contacting, and the effective amount of PS48 are as described just above. For example, in certain embodiments, the other endogenous neurotoxin is selected from the group consisting of palmitic acid and ceramide. Similarly, in certain embodiments, the effective amount is 10 nM to 100 μM. Moreover, in certain embodiments, the effective amount is at least 10 μM. And as explained above, in certain embodiments, the contacting occurs in vivo, and in certain other embodiments, the contacting occurs ex vivo or in vitro.

An aspect of the instant invention is a method of improving synaptic plasticity. The method comprises contacting a neuronal tissue with an effective amount of (Z)-5-(4-chlorophenyl)-3-phenylpent-2-enoic acid (PS48).

As used herein, "synaptic plasticity" refers to the biological process by which occurs structural and functional adaptation of neural circuits to changes in activity (such as occur in learning and memory), many environmental factors, or after several types of injury. These change the efficacy or strength in excitatory or inhibitory connections between neurons. One cellular correlate of learning and memory in mammals is long term potentiation (LTP) and long term depression (LTD). These can be measured in hippocampal or cortical brain slices as excitatory post-synaptic potentiation (EPSP) amplitudes or rate of EPSP development over time (slope). These long lasting changes in synaptic strength or cellular memory require new protein synthesis (Lynch M A Physiol Rev (2004) 84:87-136). Both pre-synaptic and post-synaptic mechanisms can contribute to the expression of synaptic plasticity.

As used herein, "neuronal tissue" refers to any tissue comprised of neurons, including, without limitation, a whole brain, a slice or slab of brain, or a brain organoid. The neuronal tissue typically will be of mammalian origin, but in certain embodiments, the neuronal tissue can be of insect, fish, amphibian, reptile, or avian origin.

In accordance with this aspect of the invention, in certain embodiments, the neuronal tissue comprises intraneuronal beta amyloid peptide A142. The intraneuronal Aβ42 can be naturally present in the tissue or it can be artificially made to be present by, for example, expression from an adenovirus or other suitable vector encoding the Aβ42.

Also in accordance with this aspect of the invention, in certain embodiments, the neuronal tissue is contacted with extracellular amyloid peptide Aβ42, for example by immersion of the neural tissue in a suitable medium comprising soluble Aβ42. It is also recognized that Aβ42 can be secreted into and internalized from the extracellular spaces.

Further in accordance with this aspect of the invention, the contacting and the effective amount of PS48 are as described just above. For example, in certain embodiments, the effective amount of PS48 is 10 nM to 100 μM. Moreover, in certain embodiments, the effective amount is at least 100 nM. Certain exemplary effective amounts of PS48 include, without limitation, 100, 120, 140, 160, 180, 200, 250, 300, 350, 400, 450, 500, 550, 600, 650, 700, 750, 800, 850, 900, 950, or 1000 nM, as well as 10, 20, 30, 40, 50, 60, 70, 80, 90, or 100 μM. As explained above, in certain embodiments, the contacting occurs in vivo, and in certain other embodiments, the contacting occurs ex vivo or in vitro.

An aspect of the instant invention is a method of improving learning and memory. The method comprises administering to a subject in need thereof an effective amount of (Z)-5-(4-chlorophenyl)-3-phenylpent-2-enoic acid (PS48).

In certain embodiments, the subject has intraneuronal beta amyloid peptide Aβ42. The intraneuronal Aβ42 can be naturally present in the tissue or it can be artificially made to be present by, for example, expression from an adenovirus or other suitable vector encoding the Aβ42.

In accordance with this aspect of the invention, in certain embodiments, the subject is a mammal. In certain embodiments, a subject is a mouse, rat, guinea pig, rabbit, cat, dog, goat, sheep, pig, horse, or cow. In certain embodiments, a subject is a non-human primate. In some embodiments, a subject is a human.

Also in accordance with this aspect of the invention, in some embodiments, the effective amount of NS48 is about 1 mg/kg/day to about 50 mg/kg/day. In various certain embodiments, the effective amount can be about 1 to about 5 mg/kg/day, about 5 to about 10 mg/kg/day, about 10 to about 15 mg/kg/day, about 15 to about 20 mg/kg/day, about 20 to about 25 mg/kg/day, about 25 to about 30 mg/kg/day, about 30 to about 35 mg/kg/day, about 35 to about 40 mg/kg/day, about 40 to about 45 mg/kg/day, or about 45 about 50 mg/kg/day. In various certain embodiments, the effective amount can be 1 to 5 mg/kg/day, 5 to 10 mg/kg/day, 10 to 15 mg/kg/day, 15 to 20 mg/kg/day, 20 to 25 mg/kg/day, 25 to 30 mg/kg/day, 30 to 35 mg/kg/day, 35 to 40 mg/kg/day, 40 to 45 mg/kg/day, or 45 50 mg/kg/day. In certain embodiments, the effective amount can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg/day.

In certain embodiments, the effective amount is at least about 10 mg/kg/day.

In certain embodiments, the administering is orally administering.

In certain embodiments, the administering is parenterally administering. For example, in certain embodiments, the administering is intravenous administration, either by injection or by infusion. In certain embodiments, the administering is intraperitoneal administration, either by injection or by infusion. In certain embodiments, the administering is by intracisternal administration, either by injection or by infusion. Yet other routes of parenteral administration are also contemplated by this aspect of the invention.

As used herein, an "effective amount" refers to an amount that is sufficient to achieve a desired effect, for example, a biological effect. In certain embodiments, an effective amount is a therapeutically effective amount. As used herein, a "therapeutically effective amount" is an amount that is sufficient to achieve a desired therapeutic effect.

An effective amount can be determined by a person of skill in the art based on any one or combination of factors, including the age, sex, size or weight, general condition, and specific condition(s) of the subject to be treated, as well as knowledge of in vitro, preclinical, and/or clinical efficacy. Preferably, an effective amount for administration to a subject is also a safe amount for administration to the subject. These factors are well known to those of ordinary skill in the art and can be addressed with no more than routine experimentation.

It should be appreciated that an effective amount does not need to restore normal levels of Akt activation and/or activity. In some embodiments, an effective amount may be an amount sufficient to reduce the Aβ-mediated inhibition of PDK-dependent activation of Akt, for example, by at least 5%, at least 10%, at least 20%, at least 30%, at least 40%, at least 50%, at least 60%, at least 70%, at least 75%, at least 80%, at least 85%, at least 90%, at least 95%, or about 100%. In some embodiments, an effective amount may be an amount sufficient to reduce the Aβ-mediated inhibition of PDK-dependent activation of Akt in a statistically significant manner.

PS48 can be combined with one or more pharmaceutically acceptable carriers and optionally one or more additional active ingredients to form compositions for use in accordance with this disclosure.

Actual dosage levels of active ingredients in the compositions of the invention can be varied to obtain an amount of the composition of the invention that is effective to achieve the desired therapeutic response for a particular subject, compositions, and mode of administration.

The selected dosage level depends upon the activity of the particular composition, the route of administration, the severity of the condition being treated, the condition, and prior medical history of the subject being treated. However, it is within the skill of the art to start doses of the composition at levels lower than required to achieve the desired therapeutic effort and to gradually increase the dosage until the desired effect is achieved. In some embodiments, lower dosages would be required for combinations of multiple compositions than for single compositions.

The compositions of the invention can be administered to a subject by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain, in the abdominal cavity, under the splenic capsule, brain, or in the cornea.

Compositions of the present invention also can be administered in the form of liposomes. As is known in the art, liposomes generally are derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p 33, et seq.

Dosage forms for topical administration of a composition of this invention include powders, sprays, ointments, and inhalants as described herein. The composition is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

In some embodiments, neurodegenerative conditions such as conditions affecting the brain may be targeted through conjugation of compounds to nanoparticles. In some embodiments a compound or drug may be targeted to the brain by inserting the compound or drug into a composition such as a wafer and adding it to the brain through surgery.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the composition, it is desirable to slow the absorption of the composition from subcutaneous or intramuscular injection. This result can be accomplished by the use of a liquid suspension of crystalline or amorphous materials with poor water solubility. The rate of absorption of the composition then depends upon its rate of dissolution which, in turn, may depend upon crystal size and crystalline form. Alternatively, delayed absorption of a parenterally administered composition from is accomplished by dissolving or suspending the composition in an oil vehicle.

Injectable depot forms are made by forming microcapsule matrices of the composition in biodegradable polymers such a polylactide-polyglycolide. Depending upon the ratio of composition to polymer and the nature of the particular polymer employed, the rate of composition release can be controlled. Examples of other biodegradable polymers include poly(orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

The invention provides methods for oral administration of a pharmaceutical composition of the invention. Oral solid dosage forms are described generally in Remington's Pharmaceutical Sciences, 18th Ed., 1990 (Mack Publishing Co. Easton, Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes a composition of the invention and inert ingredients which protect against degradation in the stomach and which permit release of the biologically active material in the intestine.

In such solid dosage forms, the composition is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In one embodiment, the excipient or carrier increases uptake of the composition of the invention, overall stability of the composition and/or circulation time of the composition in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®; (b) binders such as, for example, methylcellulose ethylcellulose, hydroxypropylmethyl cellulose, carboxymethylcellulose, gums (e.g., alginates, acacia), gelatin, polyvinylpyrrolidone, and sucrose; (c) humectants, such as glycerol; (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin; (f) absorption accelerators, such as quaternary ammonium compounds and fatty acids including oleic acid, linoleic acid, and linolenic acid; (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzethonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay; (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT®.

Examples of embedding compositions which can be used include polymeric substances and waxes.

The composition of the invention also can be in microencapsulated form, if appropriate, with one or more of the above-mentioned excipients.

Liquid dosage forms for oral administration include pharmaceutically acceptable emulsions, solutions, suspensions, syrups, and elixirs. In addition to the composition of the invention, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage.

Suspensions, in addition to the composition of the invention, can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the composition of the invention. The composition is delivered to the lungs of a mammal while inhaling, thereby promoting the traversal of the lung epithelial lining to the blood stream. See, Adjei et al., Pharmaceutical Research 7:565-569, 1990, Adjei et al., International Journal of Pharmaceutics 63:135-144, 1990, (leuprolide acetate), Braquet et al., Journal of Cardiovascular Pharmacology 13 (suppl. 5): s. 143-146, 1989, (endothelin-1), Hubbard et al., Annals of Internal Medicine 3:206-212, 1989, ($\alpha$1-antitrypsin, Smith et al., J. Clin. Invest. 84:1145-1146, 1989, (a1-proteinase), Oswein et al., "Aerosolization of Proteins," Proceedings of Symposium on Respiratory Drug Delivery II, Keystone, Colo., March, 1990, (recombinant human growth hormone), Debs et al., The Journal of Immunology 140:3482-3488, 1988, (interferon-$\gamma$ and tumor necrosis factor $\alpha$), and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

®Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a composition of the invention. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a composition of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the composition of the invention suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the composition of the invention and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the composition of the invention also is contemplated. Nasal delivery allows the passage of the composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the composition of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of the composition of the invention across cell and/or nuclear membranes, compositions of relatively high hydrophobicity are preferred. The composition of the invention can be modified in a manner which increases hydrophobicity, or the composition of the invention can be encapsulated in hydrophobic carriers or solutions which result in increased hydrophobicity.

The term "treatment" or "treating" is intended to relate to prophylaxis, amelioration, prevention and/or cure of a condition (e.g., Alzheimer's disease). Treatment after a condition (e.g., Alzheimer's disease) that has started aims to reduce, ameliorate or altogether eliminate the condition, and/or its associated symptoms, or prevent it from becoming worse. Treatment of subjects before a condition (e.g., Alzheimer's disease) has started (i.e., prophylactic treatment) aims to reduce the risk of developing the condition and/or lessen its severity if the condition does develop. As used herein, the term "prevent" refers to the prophylactic treatment of a subject who is at risk of developing a condition (e.g., Alzheimer's disease) resulting in a decrease in the probability that the subject will develop the disorder, and to the inhibition of further development of an already established disorder.

EXAMPLES

Aspects and features of the invention are illustrated by the following non-limiting examples.

Example 1

Materials and Methods

Cell Culture and Reagents

SH-SY5Y and N2a cell lines (ATCC, Manassas, VA; Sigma, St. Louis, MO) were grown in DMEM, 10% FBS, 25 mM glucose, at or below 80% confluence. SH-SY5Y were left undifferentiated. Mouse C2C12 cells (ATCC) were grown in Dulbecco's modified Eagle medium (DMEM), 20% fetal bovine serum (FBS) (Invitrogen), and maintained for passage below 60% confluence. Cultures at or above 90% confluence were then differentiated in DMEM, 2% adult horse serum (DM) for 3 days before use. Primary rat cortical neurons (PCNs) were cultured from E18 Sprague-Dawley rat fetal cortex (Charles River, Wilmington, MA) as described (Magrane et al., 2004). Briefly, isolated fetal cerebral cortex was dissociated into single cells and then seeded into 6-well plates coated with poly-D-lysine at $1 \times 10^6$ cells per well.

PCNs were cultured in neurobasal medium (Invitrogen, Carlsbad, CA) containing 2% B27 without insulin, 25 mM D-glucose, 0.5 mM L-glutamine and 1% penicillin/streptomycin for 7 days before experiments.

Antibodies used were: goat anti-Akt-1 and Actin (Santa Cruz Biotechnology); anti-p-Akt (Ser473 and Thr308), p-GSK-3α/β (Ser21/9), and GSK-3a/p (Cell Signaling); mouse anti-PDK-1 (BD Biosciences); 6E10 (Covance, Co); R1282 (gift from Dr. D. Selkoe). The GSK-3 fusion peptide (crosstide), substrate for phosphorylation, was purchased from Cell Signaling. Fluorophore-labeled Aβ42 was carboxy-fluorescein conjugated to the N' terminus (FAM-Aβ42) purchased from Anaspec (Fremont CA). Recombinant human Akt1 (inactive) and PDK-1 (active) proteins were obtained from Amsbio. PS48 ((Z)-5-(4-chlorophenyl)-3-phenylpent-2-enoic acid) and PS47 ((E)-5-(4-chlorophenyl)-3-phenylpent-2-enoic acid) were purchased from SIGMA and Axon MedChem. Dipalmitoyl-PIP3 (Matreya, State College, PA), ATP; Adenosine-5'-triphosphate (ATP), disodium salt, was supplied as a 10 mM solution in doubly distilled water (Cell Signaling). Protein A/G PLUS-Agarose (Roche). Human insulin, recombinant, dry or 10 mg/ml solution, was purchased from Sigma-Aldrich.

Infection of SY5Y and C2C12 Myotubes with Adenoviruses

Adv TetOn and TRE-Aβ42 viruses were described previously (Magrane et al., 2005). SY5Y and C2C12 myotubes were infected with Adv Aβ42/TetOn (4:1 ratio) 24-36 hr before doxycycline induction (1 µg/ml) for an additional 24-36 hr. Insulin (10 or 40 nM) was added in the last 20-30 min before harvest. PS48 (Sigma), PS47 (Axon Medchem, Reston VA), and 501-1-x compounds were added 5 min before adding insulin. Cell extracts were prepared in lysis buffer [20 mM Tris-HCl (pH 7.5), 150 mM NaCl, 1 mM EDTA, 1 mM $Na_3VO_4$, 1% NP-40, 10% Glycerol, 1 mM $Na_4P_2O_7$, 1 µg/ml Leupeptin, 1 µg/ml Pepstatin A, 1 µg/ml Aprotinin, 0.1 mM phenylmethylsulfonyl fluoride, and protease inhibitor cocktail (Roche)] and were stored at −80° C. until use.

Cell Viability

SH-SY5Y cells were washed twice in warm Dulbecco's phosphate-buffered saline (DPBS) and incubated in 1 ml DMEM containing 0.5 mg (3-[4,5-dimethylthiazol-2-yl]-2, 5-diphenyltetrazolium bromide) (MTT or WST; Molecular Probes, Eugene, OR) for 2-3 h at 37° C. and 5% $CO_2$. The medium was aspirated and the cells were washed twice with pre-warmed DPBS. The formazan salts were dissolved in 1 ml pure ethanol before use. Cells were homogenized by repetitive pipetting and centrifuged for 5 min at 4500 rpm, and the supernatant collected. Absorbance was read against an ethanol blank at 590 nm.

Aβ and ADDL Preparation

Aβ peptides were obtained from BioSource as dried trifluoroacetic acid salts. Monomeric Aβ peptides were prepared by solubilization in 5% dimethyl sulfoxide (DMSO), 25 mM Tris-HCl, pH 7.4, and used fresh or flash frozen. A$-derived diffusible ligands (ADDLs) were prepared according to Lambert et al. (Lambert et al., 1998) and Klein et al., (Klein, 2002). Briefly, Aβ peptide was dissolved in 1,1,1,3,3,3-hexafluoro-2-propanol (Sigma) and evaporated on a Speedvac. The Aβ film was resuspended in 100% anhydrous DMSO, diluted to 5 mM in F12 medium lacking phenol red (BioSource), and incubated at 4° C. for 24 to 48 hr. Following incubation and centrifugation at 14,000 g for 10 min at 4° C., the supernatant containing ADDL-enriched Aβ was transferred to a new tube.

Western Blot Analysis

Whole-cell extracts were used directly for western blot analysis (20-30 µg). Extracts from cultured cells prepared in lysis buffer, were diluted into Laemmli sample buffer, heated (95° C., 10 min), cleared by centrifugation, separated on SDS-PAGE and transferred to PVDF membrane (Immobilon-P; Millipore). Membranes were blocked in TBS containing 0.3% Tween-20 and 5% (wt/vol) non-fat dry milk. After incubation with primary antibodies (18 hr at 4° C. in buffer containing 5% bovine serum albumin (BSA) and 0.05% $NaN_3$), blots were washed and incubated in horseradish peroxidase (HRP)-conjugated secondary antibodies (1:2000 dilution; Cell Signaling). Signals were detected using ECL reagents and quantified using a Kodak Image Station 4000R.

In Vitro p-Akt and Activity Levels

Immunoprecipitations (IPs) of PDK and Akt1 were prepared from 100 µg of either SH-SY5Y, C2C12 myotubes or from insulin-treated cultures. Alternatively, commercial recombinant Akt (100 ng) and PDK (10 ng) proteins were used. PIP3 (50 nM), GSK-3 fusion protein (1 µg/50 µl, 1.0 µg), kinase buffer and Aβ peptides were added. ATP (200 µM) started the reaction (50 µl) that continued for 30 minutes at 30° C. The reaction was stopped by adding 40 µl of Laemmli buffer. 20 µl of sample was loaded onto a 10% polyacrylamide gel.

An in vitro radio assay (EMD Millipore, KinaseProfiler) was also adapted as follows. PKBα (human, recombinant, inactive, 209 nM) is incubated in 8 mM MOPS pH 7.0, 0.2 mM EDTA with 30 µM GSK3α/β consensus sequence GRPRTSSFAEGKK (SEQ ID NO: 2) and PDK1 (human, recombinant, 285 nM). β-amyloid peptide (oligomerized, 5 µM final) and PS48 were added. Final DMSO was 2%. 10 mM Mg Acetate and [$\gamma$-$^{33}$P-ATP] (specific activity approx. 500 cpm/pmol) were prepared. The reaction was initiated by the addition of the Mg ATP mix (200 µM ATP final). After incubation for 40 minutes at 37° C., the reaction was stopped by adding 3% phosphoric acid solution. 10 µL of the reaction was spotted onto a P30 filtermat and washed three times for 5 minutes in 75 mM phosphoric acid and once in methanol, prior to drying and scintillation counting.

Electrophysiology

Minor modifications were made to previous published procedures (Marshall et al., 2017; Molina-Luna et al., 2009). Deeply anesthetized rats (pentobarbital, 50 mg/kg) were decapitated, their brains quickly removed and immersed in cold (5-7° C.), oxygenated (95% $O_2$/5% $CO_2$) artificial cerebrospinal fluid (ACSF) containing: 126 mM NaCl, 3 mM KCl, 1.25 mM $NaH_2PO_4$, 1 mM $MgSO_4$, 2 mM $CaCl_2$, 26 mM $NaHCO_3$, 10 mM dextrose. Coronal slices of prefrontal cortex from day 14 rat pups (400 µm) were perfused with Aβ oligomers (40 nM) or Aβ plus PS48 (10 µM)×60 min. before applying the high frequency stimulation (HFS) protocol. Control treatment was DMSO in ACSF (artificial cerebrospinal fluid, 20 µM bicuculline). Extracellular postsynaptic field potentials were recorded using an AxoClamp2B amplifier (Axon instruments) and EX1 differential amplifier (Dagan), and digitized at 10 kHz. Data was acquired using Igor Pro (Wave Metrics) and Neuromatic (neuromatic.thinkrandom.com). The stimulus intensity eliciting 50% of the maximum amplitude (~32 µA) was used for all measurements before and after LTP induction. Baseline amplitudes were recorded for 20-30 minutes using single field stimuli applied every 30 sec to layer IV-V using concentric bipolar electrodes. Following a stable baseline period, LTP was induced by two sets of high-frequency stimulation (HFS) at 100 Hz, 60 µA (twice stimulus intensity), for 1 sec, 20 sec apart. Extracellular postsynaptic field potentials were measured from layer II-III using glass micropipettes filled with 0.9% NaCl. The amplitude rather than the slope of evoked FPs was used as a measure of the population excitatory synaptic response because in the neocortex the initial slope was contaminated by antidromic stimulation. LTP values were expressed as percentage of mean baseline EPSP±SEM. Paired two-tailed t-tests were used for statistical analysis.

Binding in Solution: Fluorescence Polarization

A procedure based on Lynch B Analytic Biochem. 247:77 (1997) was modified and adopted from Tiwari et al. (Tiwari et al., 2010). FAM-labeled Aβ42 peptide (probe) was mixed with wild type Aβ42 (1 mM total in HFIP) in a 1:2 molar ratio, evaporated to film, then solubilized to 5 mM in 100% DMSO and bath sonicated. It was then diluted to a 100 µM stock in Hams F12, pH 7.4, 2% DMSO and incubated 4° C. for 24 hrs to oligomerize Aβ (checked by western blot against 6E10 and directly by UV light-western). The recombinant protein binding targets, PDK-1 (59 kDa) or Akt-1 (60 kDa) were stocked as 500 µM. Final probe concentration was fixed at 200 nM. Final target concentrations (0-10 µM) were increased in successive samples until saturation was reached. The reaction was carried out manually in 0.6 cc quartz cuvettes (Suprasil Micro cells, 5 mm path length) for 30 min, 25° C., in 1× buffer: 100 mM NaCl, 20 mM phosphate pH 7.4, 2 mM DTT, 0.1% BSA, 2% DMSO. Final volume 600 µl. Where PS48 was added, final concentrations tested were 10, 20, and 100 µM. Absolute fluorescence polarization (FP) values were read off a LS55 PerkinElmer luminescence spectrophotometer, excit 485/emis 530 nm. FAM-Aβ42 was prepared as ADDLs and incubated with recombinant Akt-1 or PDK-1 (final [Aβ42] 200 nM, Akt from 0 to 12.5 µM). Immunoprecipitation of Aβ42 with 6E10 and western was developed with anti Akt and re-probed with R1282.

Drug Screening

Two focused libraries of PS48-family compounds were designed based on known and hypothesized structure-activity relationships and tested using an in vitro screen carried out in 48-well plates as follows (in order of rapid additions, final concentrations): 10× Kinase buffer, recombinant PDK-1 (5 µl, pre-immunoprecipitated onto agarose beads using monoclonal IgG), PIP3 50 nM, Aβ42 (as ADDL oligomers, 10 µM), recombinant Akt-1 (5 µl, pre-immuno-precipitated onto beads using polyclonal goat IgG, treated with PP2A to dephosphorylate Akt and washed), compound or PS48/PS47 (solubilized in DMSO then diluted with $H_2O$, 10 µM), ATP (to initiate Akt activation, 200 µM). Incubation proceeded for 15 min. GSK-tide (Cell Signaling) was then added and the reaction allowed to continue for 20 min more before termination in sample buffer and fractionation on SDS gel. Transfers were probed with anti-p-GSK, anti phospho-473 and -308 Akt and total Akt. The in vitro results were validated using a cell culture-based assay, as above. Briefly, adenovirus-infected PCNs (2 days) were induced with doxycycline (48 hrs) to express Aβ42. Compound was added for 12 hrs. The cells were stimulated with insulin before harvest.

Statistical Analyses

Where quantified, experiments were carried out in triplicate unless otherwise stated. Mean, standard errors and significance levels using Student's t-test were computed in Excel or Prism. In vitro Akt activation assay data (see above), in which the % inhibitory effects of Aβ42 monomers and ADDLs were tested, was fitted using a 2 site (hyperbolic), non-linear algorithm (Prism) to obtain Bmax and Kd1 equilibrium constants. Western signal intensities were all quantified by densitometry. Akt activation (phosphorylation) and activity (GSK phosphorylation) western results (stimulation or inhibition) were for the most part concordant and equivalent in fraction of change versus control. Therefore, where both endpoints were evaluated, normalized values were both included in the quantification as indicated.

Results

We had previously shown that cellular β-amyloid expression inhibits PI3K-PDK1-Akt signaling (Lee et al., 2017; Magrane et al., 2005; Suhara et al., 2003). To summarize, in vivo assays of phospho-Akt/total Akt and downstream substrate, phospho-GSK3β levels were carried out on extracts from cultured neurons exposed to an inducible adenoviral vector encoding Aβ42 (Lee et al., 2009; Magrane et al., 2005). Cells were pre-treated with insulin for 20 min prior to harvest in order to activate Akt, finding that insulin-stimulated p-Akt levels were reduced to baseline in the presence of Aβ42 expression. To confirm this, Akt enzymatic activity was measured in cell lysates using a coupled assay; immunoprecipitated (IP) Akt from insulin-stimulated cells phosphorylated a synthetic substrate peptide bearing the phosphorylation consensus sequence GSK3β fused to paramyosin (crosstide). Again, Aβ expression markedly inhibited the insulin-mediated activation of Akt. Next, an in vitro kinasd assay was developed in which immunoprecipitated or recombinant-PDK1 and Akt were mixed in the presence of activating phosphoinositide lipids and Akt substrate (GSK3β-paramyosin). Synthetic Aβ1-42 oligomers were added prior to the start of the reactions, initiated by adding ATP. 5 μM Aβ peptide inhibited the Akt-dependent phosphorylation of the target peptide, accompanied by an expected reduction in pSer473 Akt. Other data (Lee et al., 2009) indicated that Aβ inhibits the PDK-1-dependent activation of Akt by disrupting their interaction.

The pathological target identified in these in vivo and in vitro platforms suggested that a small molecule could be found that modulates the insulin-PDK-Akt activation cycle in such a way to relieve the inhibitory amyloid effect. A chemical database search brought up an allosteric activator of PDK-1 ((Z)-5-(4-chlorophenyl)-3-phenylpent-2-enoic acid; CAS 1180676-32-7, PS48), a chlorophenyl pentenoic acid having a MW of 286.7 (Engel et al., 2006) (FIG. 1). It has an inactive 'E' isomer, PS47, for control use (Hindie et al., 2009; Stroba et al., 2009). It is unique in its action to bind the hydrophobic motif/PIF binding pocket of PDK and not the ATP binding site. The compound has other possible beneficial actions that may translate to improve hippocampal neurogenesis (Zhu et al., 2010).

Figure 7A:
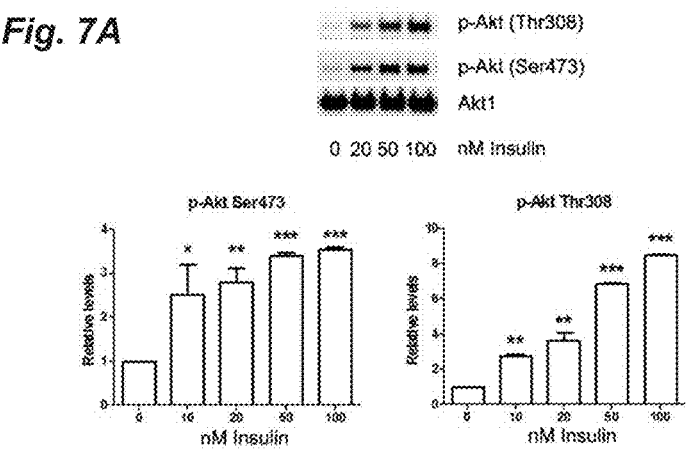
FIG. 7A. Insulin resistance in PCNs and sensitizing action of PS48. Phosphorylation of Akt was insulin-dependent in SH-SY5Y cells. Insulin was added 30 min before harvest. Near maximal responses at 50 to 100 nM.
Figure 7B:
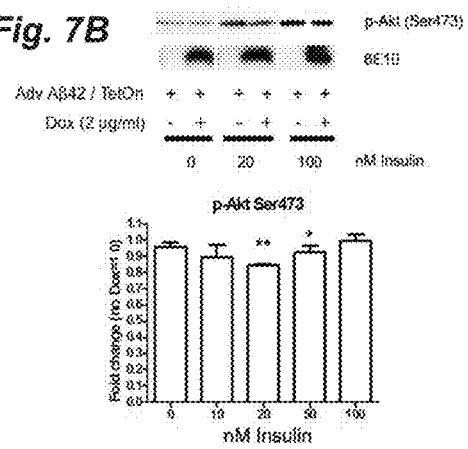
FIG. 7B. Aβ42 expression, mediated by adenovirus, inhibited insulin-stimulated Akt phosphorylation. The observed difference in phosphorylation between control (no Dox) and Aβ-expression (+Dox) was most inhibited at 20 nM insulin. However, the effect was overcome at higher doses of insulin stimulation. * $p<0.05$, ** $p<0.01$.

In the current study using the above assays, SH-SY5Y cells were used for most cell-based experiments. To model insulin resistance in these cells, Akt (PKBα) activation with increasing insulin concentrations was established (FIG. 7A). Then at the same varying doses, cellular expression of Aβ42 was introduced to produce insulin resistance. At moderate insulin doses (20 nM), Akt activation was inhibited by Aβ42, whereas high doses of insulin (100 nM) overcame the effect. Thus Aβ42 was shown to desensitize insulin action, raising the insulin concentration threshold to achieve an equivalent response (FIG. 7B).

Figure 7C:
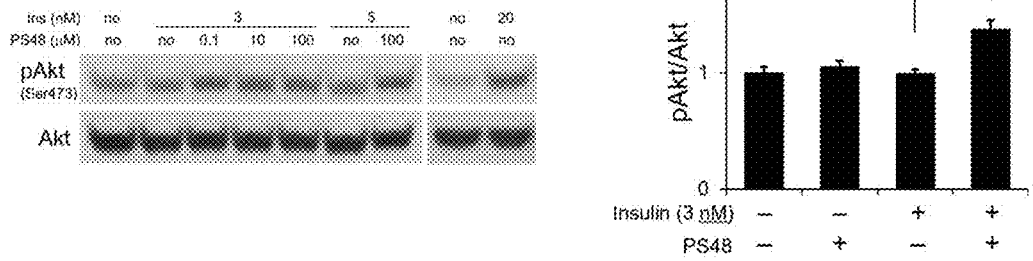
FIG. 7C. At subthreshold insulin doses (3 nM, 15 min, 10% serum) in N2a cells, PS48 (0.1 to 100 μM, 2 hrs) was an insulin sensitizer, boosting the phosphorylation of Ser 473 to a 20 nM insulin-equivalence response. N2a cells, n=3. Quantified results shown in graph at right.
Figure 7D:
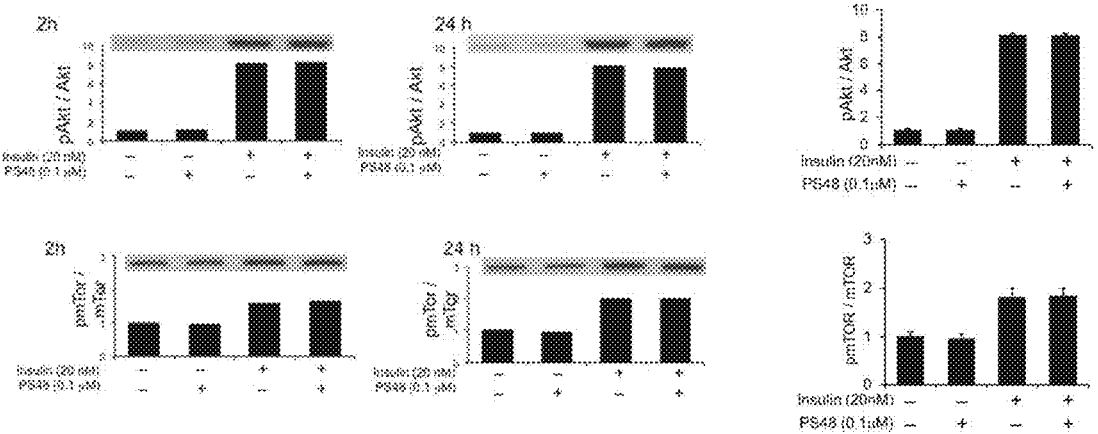
FIG. 7D. PS48 at doses from 0.01 to 100 μM for 2 hrs or 24 hrs did not over-activate Akt Ser473 or affect mTOR Ser2448 phosphorylation in rat primary cortical neurons stimulated with submaximal 20 nM insulin (15 minutes prior to lysis). Western blots shown above and corresponding quantified results shown below. n=2.

To characterize PS48, we found that it did not intrinsically activate basal Akt. However, in the presence of low dose insulin (3 nM), where Akt activation is subthreshold, PS48 augmented the response. This in keeping with its purported allosteric action to positively modulate PDK activity. (FIG. 7C). At moderate insulin doses, that produce robust Akt phosphorylation, PS48 did not further enhance it. Neither did PS48 intrinsically affect at least one critical downstream factor in this pathway, mTOR, nor did it override insulin action. (FIG. 7D). These properties make it ideal to test if it will protect insulin signaling against amyloid peptide toxicity, while not over-regulating the pathway.

PS48 was tested in cultured neuronal SH-SY5Y cells, where it was shown to reverse β-amyloid expression-induced inhibition of Akt activation (pT308 phosphoryation) (FIG. 1A). Notably, it did not overactivate basal levels of phosphoAkt to a statistically significant extent. Cells were pre-treated with either PS48 (1 μM) or high dose insulin (100 nM) for 2 hrs before doxycycline was added. Aβ42 expression proceeded over the next 46 hrs. Insulin had similar protective action compared to PS48 for the duration of expression. pAkt levels were quantified densitometrically, shown in FIG. 1A. To confirm, Akt enzymatic activity to phosphorylate a consensus substrate peptide corresponding to phopho-Ser21/9 sites on GSK3-α/β was tested. The same outcome was observed, mainly that PS48 (50 nM) protected Akt activity from inhibitory cellular Aβ42 expression.

The effect of PS48 to reverse a non-amyloid dependent model of insulin pathway toxicity, exposure to the long chain saturated fatty acid, palmitate, in rat primary cortical neurons, was also tested. As shown in FIG. 1B, low dose insulin (20-40 nM) given just 20 min prior to harvest, stimulated Akt phosphorylation, which palmitate (300 μM) partly blocked (~30%). PS48 significantly reversed some of this inhibition.

In FIG. 1C, various doses of PS48 (0.1, 1.0, 10 μM) were tested in both SH-SY5Y and C2C12 myotube cell lines. A dose-dependent effect to reverse Aβ42-provoked inhibition of insulin-stimulated Akt phosphorylation became apparent at 100 nM (p<0.01).

Several downstream effectors and substrates of Akt were examined for sensitivity to Aβ toxicity and PS48 effects focusing on CREB, the cAMP response element binding transcription factor. CREB has pleiotropic actions to promote neuronal survival, progenitor proliferation, neurite outgrowth, and differentiation. It is also well documented to control the activity-driven and neurotrophin-dependent expression of proteins essential to long term memory (LTM) formation and synaptic plasticity (LTP) (see reviews by (Alberini, 2009; Benito & Barco, 2010; Carlezon et al., 2005)). It is situated in the PI3K/Akt/CREB pathway to transduce effects of insulin, IGF-1 and BDNF on protein expression critical to neurogenesis and plasticity (Barco & Marie, 2011; Leinninger et al., 2004; Peltier et al., 2007). CREB supports LTM by stabilizing synaptic strength, regulating intrinsic neuronal excitability, and recruiting subsets of neurons in the hippocampus and amygdala that encode the memory trace (Josselyn et al., 2001; Lisman et al., 2018; Restivo et al., 2009; Sekeres et al., 2010). CREB was selected for study because it can be directly activated by Akt (Brami-Cherrier et al., 2002; Li et al., 2011), it is protective against neuronal apoptosis (Bonni et al., 1999; Walton et al., 1999), and it supports LTP (Barco et al., 2002). Results demonstrated consistent inhibition of insulin-stimulated CREB phosphorylation (pS133) by intracellular Aβ42 and this was also reversed by PS48 (50 nM) (FIG. 8A).

Previous work had also shown sensitivity of endogenous GSK3α/β (inhibitory S9A phosphorylation) to viral-expressed Aβ42 (Magrane et al., 2005), however the current experiments under combined Aβ42 and PS48 pressure proved inconclusive. Nevertheless, results from the present study showed that PS48 had no effect on resting cellular pGSK levels (FIG. 8B). Finally, in testing for changes in activating phospho-levels of indirect downstream substrate and metabolic sensor mTOR, results showed that neither Aβ expression nor PS48 application had any effect (FIG. 8C).

Figure 2B:
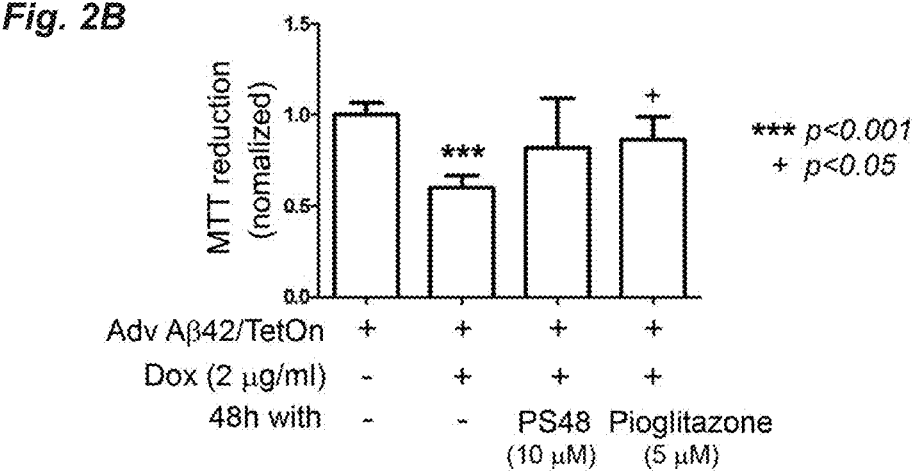
FIG. 2B. PS48 (10 µM) compared favorably with PPAR agonist pioglitazone (5 µM).
Figure 2C:
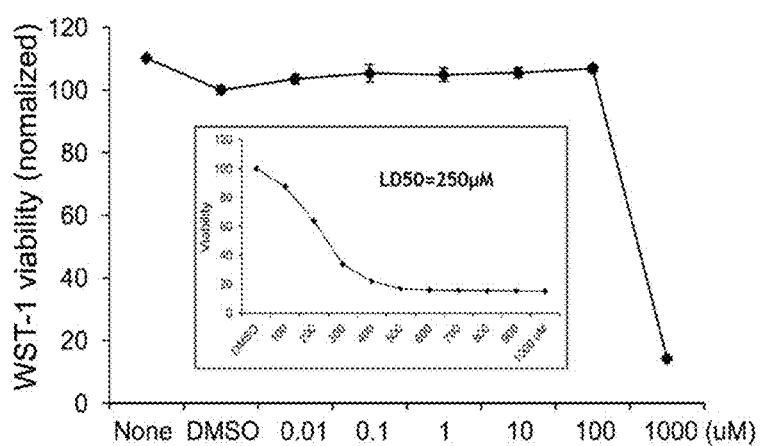
FIG. 2C. Toxicity profile of PS48 itself determined in a similar reduction assay (WST-1) was well tolerated by cells (LD50=250 µM). Inset, linear representation.

In parallel experiments, PS48 pretreatment also restored the Aβ-induced decrement in cell viability. For example, FIG. 2A shows MTT reduction to formazan assay, bars 6 vs 2. SH-SY5Y cells were exposed to Adv TRE-Aβ±doxycycline to induce Aβ42, then harvested at 48 hrs. Amyloid-bearing cells were less viable compared to control (bar 2 vs control bar 1; p<0.01). Pretreatment of cultures (before doxycycline) with high dose insulin (100 nM) or PS48 (10 μM) revered cells to basal condition or better (bars 4 and 6 vs con, p<0.05). The same cytoprotection was obtained in C2C12 myotubes. As shown in FIG. 2B, PS48 also compared favorably with a PPAR agonist, pioglitazone. The toxicity profile of PS48 itself was determined in a similar reduction assay (WST-1) and was found to be well-tolerated by cells (FIG. 2C, LD50 250 μM).

Figure 3A:
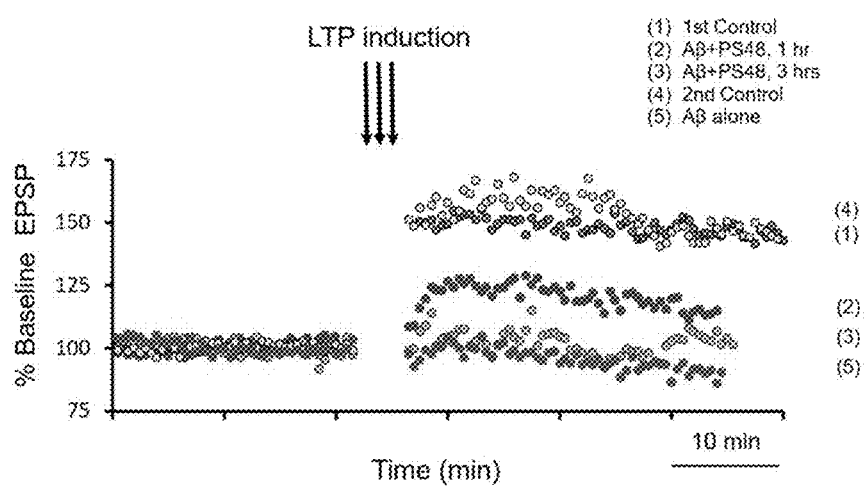
FIG. 3A. PS48 partially reversed inhibition of long term potentiation (LTP) caused by oligomers of synthetic Aβ42 peptide. Acute prefrontal rat cortical slices were superperfused with Aβ42 peptide (0.5 µM) prepared as amyloid diffusible ligands (ADDLs), that are largely comprised of oligomeric species. LTP was measured as % baseline excitatory postsynaptic potential (EPSP) amplitudes. LTP was completely abrogated by all concentrations of Aβ42>1 nM (2.5-500 nM; (5)). PS48 (10 µM) significantly improved LTP at the 1 hour mark (2) after Aβ42 application. Washout restored LTP (4).
Figure 3B:
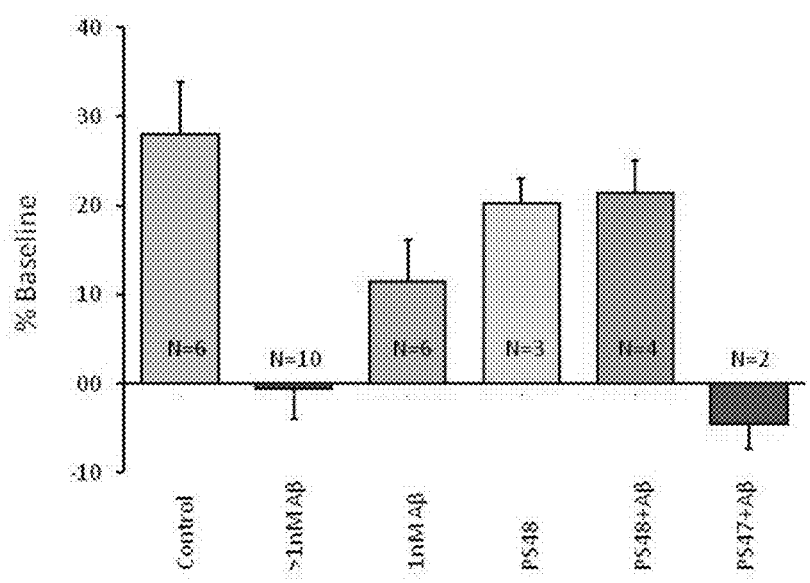
FIG. 3B. PS47, an inactive isomer control, had no effect on LTP.

PS48 was further tested in vivo and found to partially reverse the inhibition of long term potentiation (LTP) caused by oligomers of synthetic Aβ42 peptide (FIG. 3A). Acute prefrontal rat cortical slices were super-perfused with Aβ42 peptide (0.5 μM) prepared as amyloid diffusible ligands (ADDLs), that are known to be largely comprised of oligomeric species. LTP was measured as % baseline excitatory postsynaptic potential (EPSP) amplitudes. LTP was found to be completely abrogated by all concentrations of Aβ42>1 nM (2.5-500 nM). PS48 (10 μM) significantly improved LTP at the 1-hour mark after Aβ42 application. By 3 hours, however, the beneficial effect had disappeared. Washout restored LTP. PS47, an inactive isomer control for PS48, was found to have no effect (FIG. 3B).

Figure 4A:
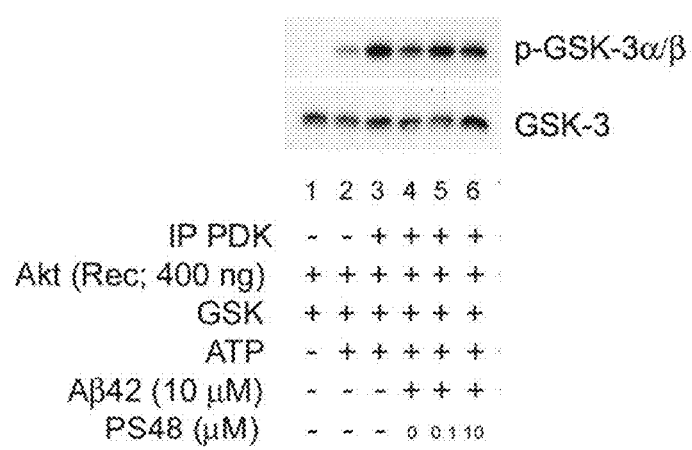
FIG. 4A. PS48 was active at 0.1 and 10 µM in reversing the inhibition of GSK consensus peptide phosphorylation. Recombinant Akt and PDK-1 proteins were added to a reaction mixture containing synthetic Aβ42 peptide oligomers (10 µM) and ATP to start the reaction. A GSK fusion peptide was added as substrate for the enzymatic readout (phospho-S9 GSK3a/p).
Figure 4B:
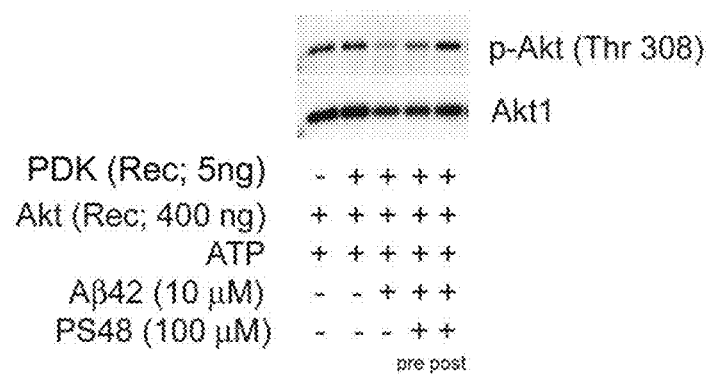
FIG. 4B. PS48 (100 µM) also restored Akt activation (pT308 levels) in the presence of Aβ42, fully if added after (post) and partially if added before (pre) Aβ peptide.
Figure 4C:
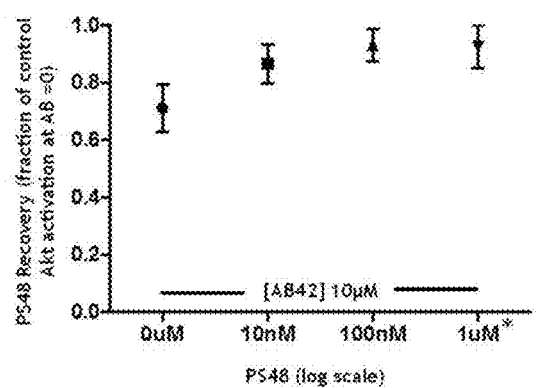
FIG. 4C. Pooled quantitative results from FIGS. 4A and 4B. In the presence of 10 µM Aβ42, ~30% of Akt activation was inhibited (expressed as fraction of control, i.e., absent Aβ42 (0.70±0.09). Beginning at 10 nM PS48, activation/activity was increasingly restored until a maximum of 0.95±0.08 of control was reached at ≥0.1 µM PS48 (includes 10 and 100 µM data points) (n=6 ea).

PS48 was then tested in an in vitro assay of both Akt activation (phosphorylation of T308) and enzyme activity. As shown in FIG. 4A, recombinant Akt and PDK-1 proteins were added to a reaction mixture containing synthetic Aβ42 peptide oligomers (10 μM) and ATP to start the reaction. Some experiments employed added PI3P and/or pre-deactivating Akt by treatment using protein phosphatase 2a (PP2A) with variable improvements in the efficiency of activation. A GSK fusion peptide was added as substrate for the enzymatic readout (phospho-S9 GSK3α/β). PS48 was found to be active at 0.1 and 10 μM in reversing the inhibition of GSK phosphorylation. PS48 (100 μM) also restored Akt activation (pT308 levels) in the presence of Aβ42, fully if added after (post) and partially if added before (pre) application of Aβ peptide (FIG. 4B). The pooled results were quantified and shown in FIG. 4C. In the presence of 10 μM Aβ42, ~30% of Akt activation was inhibited (expressed as fraction of control, i.e., absent Aβ42 (0.70±0.09). Beginning at 10 nM PS48, activation/activity was increasingly restored until a maximum of 0.95±0.08 of control was reached at ≥1 μM PS48 (includes 10 and 100 μM data points) (n=6 ca).

Figure 5A:
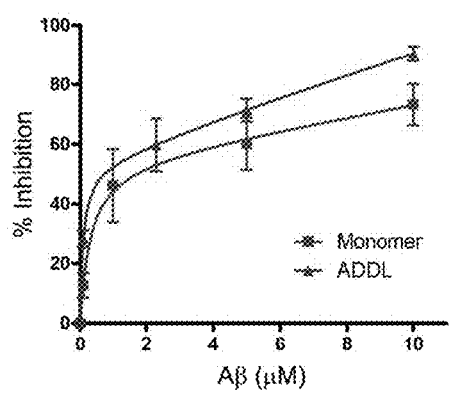
FIG. 5A. Aβ42 monomers and ADDL-oligomer preparations, at concentrations shown, exhibited saturation effects to inhibit the activation of Akt by PDK-1. In vitro assay data are presented as % inhibition of either activation of Akt by PDK-1 (phospho-T308) or of its subsequent activity to phosphorylate a GSK3β consensus peptide fused to paramyosin ("crosstide"). Densitometry results from both western blots were combined. Bmax~52% for both A3 preparations: ADDL, Kd1=0.08 µM; monomers, Kd1=0.31 µM. n=2-7 experiments each point, ±1 SEM (standard error of the mean).

To further explore target engagement, the characteristics of Aβ42 interaction with PDK-1 and/or Akt-1, upon which the beneficial actions of PS48 are supposed, were probed. Equilibrium Aβ42 dosage and binding experiments in solution to the respective kinases were conducted. First, the in vitro paradigm above was used to test whether Aβ42 peptide exhibits dose-dependent saturation effects on the activation (phosphorylation of T308) and enzymatic activity of Akt (to phosphorylate its consensus substrate). The combined densitometry data shown in FIG. 5A suggests that either Aβ monomers or oligomers bind in a saturable manner to either one or both of its targets (PDK-1, Akt-1), individually or in complex. Using a 2-site, non-linear fit algorithm, a Bmax value of ~52% inhibition of control activation was obtained for both species, however the oligomers showed greater affinity (ADDLs: Kd1=0.08 μM, monomers: Kd1=0.31).

Figure 5B:
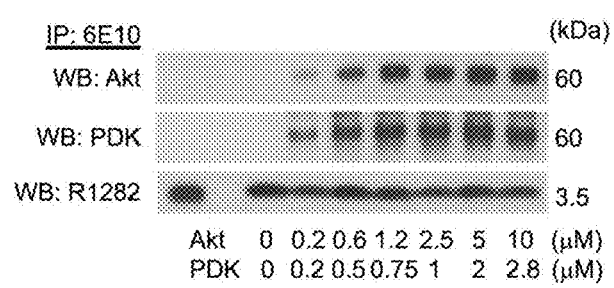
FIG. 5B. Direct binding of recombinant PDK-1 and Akt-1 to Aβ42 in solution had saturation characteristics. Aβ42 was immunoprecipitated (6E10), fractionated by Western and co-precipitates detected using anti-Akt and anti-PDK. Aβ42 concentration was fixed at 200 nM and detected using polyclonal R1282.
Figure 5C:
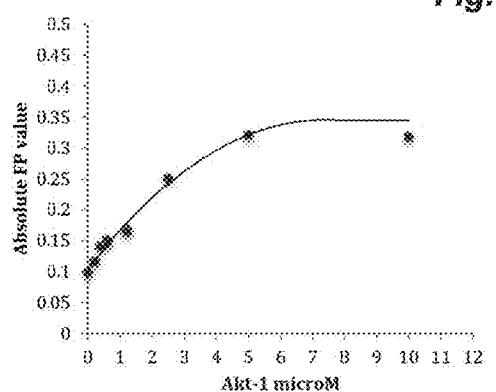
FIG. 5C. Quantification of Aβ42 binding to Akt-1 as measured by fluorescence polarization (FP). The probe was FAM-tagged-Aβ42. Recombinant kinase titration shown along X-axis. The spectrophotometric polarization signal increased as the probe became more restricted by receptor binding. Bmax: 0.32; IC50: ~2 µM.
Figure 5D:
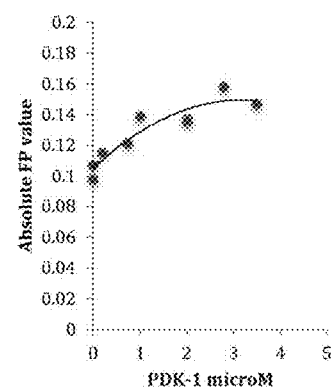
FIG. 5D. Quantification of Aβ42 binding to PDK-1 as measured by fluorescence polarization (FP). The probe was FAM-tagged-Aβ42. Recombinant kinase titration shown along X-axis. The spectrophotometric polarization signal increased as the probe became more restricted by receptor binding. Bmax: 0.16; IC50: ~1 µM.
Figure 5E:
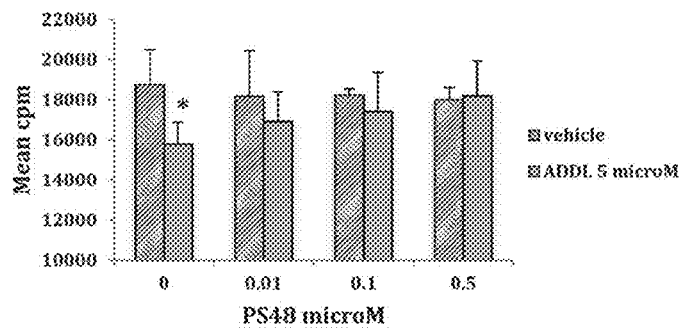
FIG. 5E. PS48 at 10 nM, increasing doses to 0.5 µM, restored phosphorylation of GSK peptide (measured in counts per minute) in presence of 5 µM Aβ42 (ADDL). *p<0.05 vs vehicle.

To independently confirm the reversal of the PDK/Akt activation sequence by Aβ42 peptide, a modified radiolabel-based assay was employed. Again, PS48 dose-dependently reversed the inhibition of $P^{32}$-labeled phosphate addition to consensus peptide. The effect was first noticed at 10 nM (FIG. 5B). Next, a novel assay using a fluorescence polarization (FP) technique was used to determine if Aβ42 bound to either PDK-1 or Akt-1 in solution and to discern any effect of PS48 on this. In this assay a spectrophotometric filter detects the fluorescent signal from a probe that becomes polarized once restricted by receptor binding. Results indicated that the FP signal increased as the concentration of either recombinant PDK or Akt were increased. The probe concentration (fluorescein amidite (FAM)-tagged-Aβ42=200 nM) was fixed in this procedure. Results shown in FIG. 5C are from 2 experiments. Saturable binding to Aβ was shown by both target molecules, where the Kd (½ max constant) for PDK showed slightly increased affinity over Akt, but fewer binding sites (FIG. 5C). PS48 additions did not affect either polarization signal, indicating that Aβ42 is probably not competitively occupying the pocket site (results not shown). The in-solution FP assay was validated by co-immunoprecipitating the bound products. IP of FAM-labeled Aβ42 with anti-Aβ42 6E10 pulled down increasing amounts of Akt and PDK according to the titration until saturation (FIG. 5D). Aβ42 concentrations in all reactions were constant, as expected from the input, reflected in the equal signals across the anti-R1282-developed blot shown in FIG. 5D.

Drug screening experiments were performed using a focused library of novel compounds that were synthesized using PS48 as the starting scaffold. Two generations were created based on structure-activity relations (SAR) in an attempt to optimize performance. The quantified results of western-based in vitro assays, compared to PS48, are shown in Table 1.

TABLE 1

| number | fraction of control activity Aβ 42 = 0.62 (.16) | fraction recovery from Aβ-induced inhibition Aβ 42 = 0.00 (.01) |
|---|---|---|
| PS48 | 0.95 (.04) | 0.83 (.18) * |
| 508-1-7 | 0.97 (.10) | 0.98 (.23) * |
| 508-1-11 | 0.79 (.17) | 0.53 (.38) |
| 508-1-9 | 0.74 (.11) | 0.23 (.36) |
| 508-1-21 | 0.59 (.15) | 0.13 (.35) |
| 508-1-23 | 0.83 (.19) | 0.74 (.43) |
| 508-1-25 | 0.99 (.07) | 0.99 (.26) * |
| 508-1-5 | 0.85 (.09) | 0.43 (.35) |
| 508-1-27 | 0.91 (.14) | 0.85 (.66) |
| 508-1-29 | 0.77 (.09) | 0.14 (.32) |
| 508-1-31 | 0.95 (.11) | 1.00 (.29) * |

Activity of first generation PS48 analogs

| number | fraction of control activity Aβ 42 = 0.72 (.05) | fraction recovery from Aβ-induced inhibition Aβ 42 = 0.00 (.01) |
|---|---|---|
| 508-1-66 | 0.82 (.05) | <0 |
| 508-1-72 | 0.89 (.05) | <0 |
| 508-1-67 | 0.89 (.07) | 0.45 (.29) |
| 508-1-75 | 0.86 (.06) | 0.01 (.52) |
| 508-1-60 | 0.75 (.04) | <0 |
| 508-1-62 | 0.80 (.05) | <0 |
| 508-1-64 | 0.86 (.07) | 0.47 (.52) |
| 508-1-68 | 1.02 (.06) | 1.50 (.50) * |
| 508-1-73 | 0.87 (.05) | <0 |
| PS48 | 0.88 (.06) | 0.51 (.27) * |
| PS47 | 0.75 (.02) | <0 |

Activity of second generation PS48 analogs

The structure of each compound tested is shown below in Table 2.

TABLE 2

| Structure | Compound Number | Molecular Weight |
|---|---|---|
| [structure drawing] | 508-1-7 | 329.82 |

TABLE 2-continued

| Structure | Compound Number | Molecular Weight |
|---|---|---|
| (structure) | 508-1-25 | 343.8 |
| (structure) | PS48 | 286.75 |
| (structure) | 508-1-31 | 335.21 |
| (structure) | 508-1-68 | 357.83 |

Figure 6A:
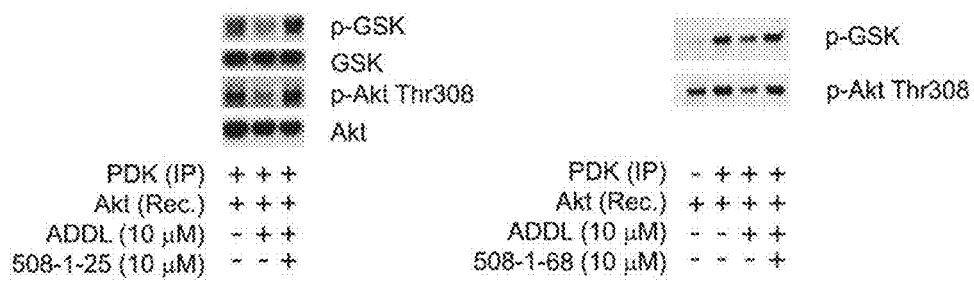
FIG. 6A. Selected Westerns of in vitro reaction mixture by products, GSK peptide and Akt T308 phosphorylations. Representative PS48 analog compounds 508-1-60 and 508-1-75 (2nd generation) shown were inactive. Compounds 508-1-7 ($1^{st}$ generation), 508-1-25 (1st generation), and 508-1-68 (2nd generation) restored activation as well as or better than PS48. See Table 1.
Figure 6B:
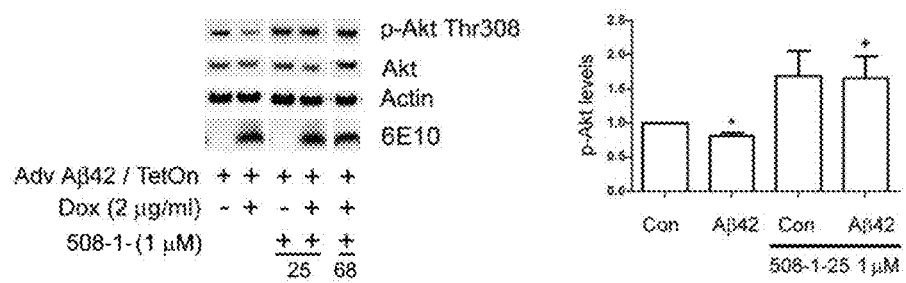
FIG. 6B. In vivo verification studies in SH-SY5Y cells. Addition of doxycycline resulted in intracellular amyloid accumulation (6E10 blots). Phospho-Akt levels, both T308 (shown) and S473 (not shown) were quantified and pooled for the bar graphs. All cultures were stimulated with insulin (40 nM, 240 ng/ml) in the last 20 minutes of the Aβ expression period. n=3 experiments. Representative blots of active compounds 501-1-25 and 508-1-68 (1 μM) are shown and quantified. * $p<0.05$ vs control (Con); +$p<0.01$ vs Aβ42. See Table 1.

The activity of each compound against the Aβ42 effect to inhibit the PDK-Akt activation sequence is shown in Table 1 as two indices: 1) fraction of the control activity (normalized to 1.00), or residual, after inhibition by the addition of Aβ42 alone (0.62±0.16), and 2) fraction of any recovery to control level from Aβ42-induced inhibition (set at 0.00). With either index, a value of ≥1.00 is a complete reversal. Based on this data a rough SAR is beginning to emerge where it appears that the greatest effect is realized by modifying the acidic portion of PS48, e.g., extension from the linker and aryl groups. An increase in potency over PS48 was achieved with compounds 508-1-7, 508-1-25, 508-1-31, and 508-1-68. Examples of in vitro assay performance are shown in FIG. 6A and FIG. 6B for compound 508-1-25 (generation 1) and compound 508-1-68 (generation 2). These were then validated as correcting the inhibition of Akt phosphorylation in the cell-based model of Aβ toxicity (as in FIG. 1), shown at FIG. 6B, right. The new "hit" compounds also had no direct or indirect effects on potential downstream off-targets such as mTOR (protein levels and phosphorylation status, results not shown). Moreover, the LD50 of several compounds in N2a neural cultures proved even higher than PS48 (e.g., 508-1-25, 350 μM, WST assay, result not shown).

DISCUSSION

Akt (PKB) is an essential kinase in the insulin/IGF signal cascade having pleotropic influence over many cell survival and metabolic pathways. Its crystalline structure in complex with a substrate peptide (GSK3β) and ATP analog, reveals the structural relationship between the C-terminal hydrophobic motif (HM) and the activating phosphorylation of Akt on the Thr 308 residue by PDK-1 (Yang et al., 2002). The crystal structure of PDK-1 in complex with ATP reveals the HM-binding pocket (PIF domain located on the N terminus) and phosphoSer-binding pocket through which it docks with its many substrates including: Akt, SGK, S6K, PKC and RSK (Biondi et al., 2002). Interestingly, Akt is the only substrate not requiring docking at the PIF-pocket site to undergo catalytic activation by PDK-1 (Biondi et al., 2001; Collins et al., 2003). PS48 and family of small molecule ligands are allosteric activators of PDK-1, binding within the PIF pocket (Stroba et al., 2009), thereby facilitating Akt activation by IGF-1 (Biondi et al., 2000; Engel et al., 2006; Hindie et al., 2009); for review see Xu et al. (Xu et al., 2019). Additional actions include supporting induction of pluripotent stem cells from somatic cells (Zhu et al., 2010).

PS48 action was characterized in the context of insulin signaling using a neuronal cell model system, demonstrating its beneficial ability to reverse Aβ42 oligomer-induced insulin resistance and toxicity. First, a dose dependency of Akt activation by insulin in PCN and N2a cultures was established. Intracelluar expression of Aβ42 oligomers resulted in a reduction of sensitivity to insulin, such that higher insulin doses were required to overcome the resistance. At low, subthreshold doses of insulin (3 nM), PS48 pretreatment appeared to sensitize Akt activation. Next, PS48 (0.1 to 1 μM) was shown to reverse the inhibitory effect of Aβi expression on submaximal insulin-induced Akt phosphorylation, similar to the effect of a higher insulin dose (100 nM) alone. The same findings were obtained in another insulin-responsive cell line, C2C12 myotubes. Moreover, PS48 partially overcame insulin resistance in a non-amyloid model of cellular toxicity, to the saturated fatty acid palmitate. A downstream effector and substrate of Akt, CREB, was also hypophosphorylated after Aβ expression, and accordingly corrected by treatment with PS48. In contrast, another effector, phospho-mTOR, remained unaffected by either treatment. The lead compound PS48 furthermore reversed Aβ-induced cell death in a neuroblastoma cell line, as did high dose insulin and pioglitazone treatments. It also reversed the effect of synthetic Aβ peptide (ADDL oligomers) to inhibit LTP in rat prefrontal cortical slices.

To test the purported cellular step involved in this mechanism of insulin resistance, in vitro reactions were performed using recombinant Akt and constitutive active PDK kinases to phosphorylate a GSK3α/β-based consensus peptide substrate. Aβ oligomers (ADDLs) inhibited Akt activation and crosstide phosphorylation, and PS48 (10 nM to 1 μM) restored this to 90% of control levels. Mechanistically, Aβ42 was shown to bind to both recombinant Akt and PDK using an in-solution fluorescence polarization assay, the two kinases having different affinities and saturation levels. Finally, in vitro and cell-based assay platforms were employed in a focused medicinal chemistry effort to probe structure-activity characteristics of the parent molecule. Other analogs were found that reversed the inhibited Akt activity by better than 90%.

The two main physiological readouts of Aβi toxicity in this study that were reversed by PS48 were cell death and inhibited synaptic plasticity (LTP). Results disclosed herein show that PS48 and analogs in development restored Akt activation by insulin when inhibited by Aβi accumulation. Akt is critical to both neuronal survival (Dudek et al., 1997) and LTP as demonstrated in prefrontal cortex, amygdala and hippocampus (Lai et al., 2006; Lin et al., 2001; Pen et al., 2016). Hippocampal LTP is particularly sensitive to Aβ oligomers (Jo et al., 2011; Townsend et al., 2007). Among its possible effectors in these two outcomes, the CREB link appears to be implicated here because this result mirrored the Akt responses to Aβi and PS48 (FIG. 1). CREB is activated by several canonical receptor-activated kinase pathways (e.g., PKA, CaMK, MAPK). In particular, BDNF/TrkB receptor activation has been well studied (Alonso et al., 2002; Pizzorusso et al., 2000; Tao et al., 1998). However, insulin and IGF-1 also phosphorylate CREB via PI3K/Akt (Leinninger et al., 2004), and as mentioned, this can occur directly (see also Du & Montminy, 1998; Pugazhenthi et al., 1999). Another effector intervening between PT3K/PDK/Akt and CREB is GSK3αβ. Akt stimulation results in GSK3 inactivation, resulting in CREB de-repression (via inhibitory pS129: Grimes & Jope, 2001; Horike et al., 2008). Moreover, GSK3 activation promotes apoptosis (Beurel & Jope, 2006; Hetman et al., 2000) and depresses spatial learning and LTP in mice (Dewachter et al., 2009; Hernandez et al., 2002). Although results disclosed herein were inconclusive on cellular GSK, the Akt activity assay data could still be consistent with a partial role for this mechanism.

Published studies have been mixed with respect to the state of Akt activation in AD brain and models, reporting either over- or under-phosphorylation or activity. Far fewer reports specifically address the 3-phosphoinositide-dependent kinase, PDK-1, in AD or neurodegeneration. Pietri and colleagues (Ezpeleta et al., 2019; Pietri et al., 2013) found PDK-1 activity increased in neurons infected with prion protein PrPSc or in transgenic mice affected by β-amyloid pathology, as well as in AD brain. In a novel but complicated mechanism, PDK-1 overactivation is held responsible for loss of TACE-mediated APP and PrPc α-secretase cleavages, from accelerated TACE internalization. The result is an over-production of Aβ and TNF-mediated neurotoxicity and memory deficit. Accordingly, PDK-1 silencing or inhibition restored survival and memory and reversed pathology parameters. Both PrPSc and Aβ were hypothesized to stimulate PrPc to recruit Src and PI3K kinases to overactivate PDK-1. The relevance of these changes to the insulin/Akt axis was not explored. Notably however, a PrP Sc-like peptide (106-126) inactivated Akt and caused death in SH-SY5Y and primary granule cells, outcomes confirmed in a PrPSc-infected mouse model. These were reversed by constitutive activation of Akt or insulin treatment (Simon et al., 2014).

It remains plausible but clinically untested if a strategy to restore Akt responsiveness to insulin has value in prevention or treatment of AD. Based on the data disclosed herein targeting the PDK-Akt activation sequence with PS48 or an allosteric ligand based on its structure may be a viable candidate. Importantly, PS48 does not itself over-stimulate normal insulin signaling in PCNs, nor does it over-activate basal Akt, lessening potential oncogenesis concerns (Adamo et al., 2011; Lo, 2010). Notably, PS48 was not toxic to cells (LD50=25 μM). This is possibly due to the purported allosteric modulatory action of this compound, as well as found in various other drugs of this class (Brotz-Oesterhelt et al., 2005; Zorn & Wells, 2010). Other bi-aryl, halogenated carboxylic acids have a safe record in humans, for instance Tolfenamic acid, used for the treatment of migraines (Hansen, 1994; Liggett et al., 2014).

In support of efforts to facilitate Akt/PDK signaling, other interventions have had similar action on the insulin/Akt transduction pathway to mitigate Aβ toxicity. For instance, α7nAcR stimulation (nicotine on PCNs) activates PI3K and pAkt to block AD-mediated enhancement of mitochondrial AIF release/nuclear translocation (Yu et al., 2011), as well as block Aβ-mediated glutamate toxicity and prevent mitochondrial apoptosis (Kawamata & Shimohama, 2011; Kihara et al., 2001; Shimohama & Kihara, 2001). Some studies favor insulin sensitizing PPAR-gamma agonists such as pioglitazone and rosiglitazone, that target genes such as IRS-1, GLUT-4, and PI3K (Kintscher, 2008; Miller el al., 2011), for the treatment of AD and MCI, in particular with co-morbid diabetes (Liu et al., 2015). For instance, rats experimentally made brain insulin resistant with i.e.-streptozotocin and given one dose i.p. of PPAR-δ agonist showed prevention of deficits in learning and memory, insulin receptor mRNA/ChAT mRNA, and insulin binding to IR (de la Monte et al., 2006). We also note with interest several recent reports that direct pharmacological activation of Akt in Aβ-injected and in 5×FAD AD mice, resolved memory impairments and synaptic LTP deficits and restored inhibited Akt to control levels (Yi et al., 2018). Activation of Akt/PI3K in primary mouse neurons also proved protective against transfected mutant APP and improved locomotor activity in an Aβ42-*drosophila* model (Zhang et al., 2016).

Figure 9:
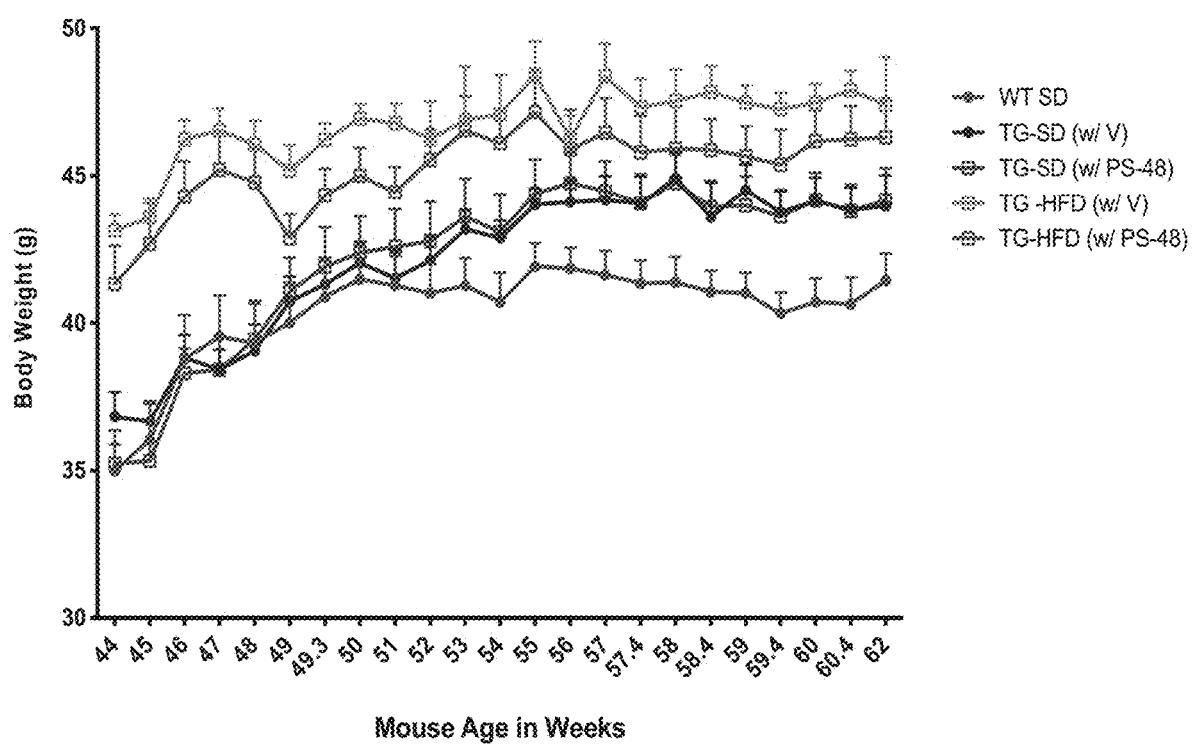
FIG. 9. Body weights over time. Data are mean±SEM. HFD, high fat diet; SD, standard diet; TG, transgenic; V, vehicle; WT, wild-type.

Example 2. PS48 Improves Spatial Learning and Memory in a βAPP/PS-1 Transgenic Mouse Model of Alzheimer's Disease Beginning at age 44 weeks, wild-type (WT) and transgenic (TG) mice on standard diet or high fat diet (HFD) and with PS48 or vehicle treatment via diet were weighed weekly for 18 weeks. As shown in FIG. 9, the mean weight for each group at the onset of PS48 or vehicle treatment via diet was WT on standard diet, 35.0±1.36 g; TG on standard diet with vehicle, 36.83±0.84 g; TG on standard diet with PS48, 35.24±0.66; TG on HFD with vehicle, 43.14±0.54 g; and TG on HFD with PS48, 41.32±1.29 g. Animals on HFD by 44 weeks were obese but had normal activity levels.

Figure 10E:
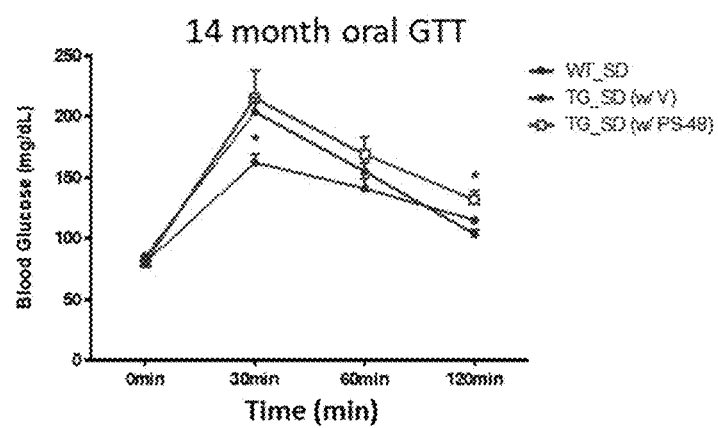
FIG. 10E. Oral glucose tolerance test for different groups of mice at 14 months of age. SD, standard diet; TG, transgenic; V, vehicle; WT wild-type.

At 6 months, both WT and transgenic mice on HFD trended toward higher fasting blood glucose, p=0.0324, F3, 36=3.26 ANOVA, however between-group t-tests were not significant. The TG groups (HFD and standard diet) had slightly prolonged oral glucose tolerance test (OGTT) levels. See FIGS. 10A and 10B.

At 12 months the HFD TG group began to show some dysregulation of expected glucose control, with a lowering of fasting glucose and OGTT responses (p=0.0092, F(3,32)=4.54, t-tests were not significant between groups. See FIGS. 10C and 10D.

At the end of phase 2 (active drug) trial, OGTT was administered to the standard diet animals. Animals were approximately 15.5 months at the time of the assay. The APP/PS-1 TG vehicle-treated mice on standard diet had a blunted response to glucose challenge, particularly at the 30 min time point. PS48 helped to normalize the glucose response. *p<0.05. See FIG. 10E.

Figure 11A:
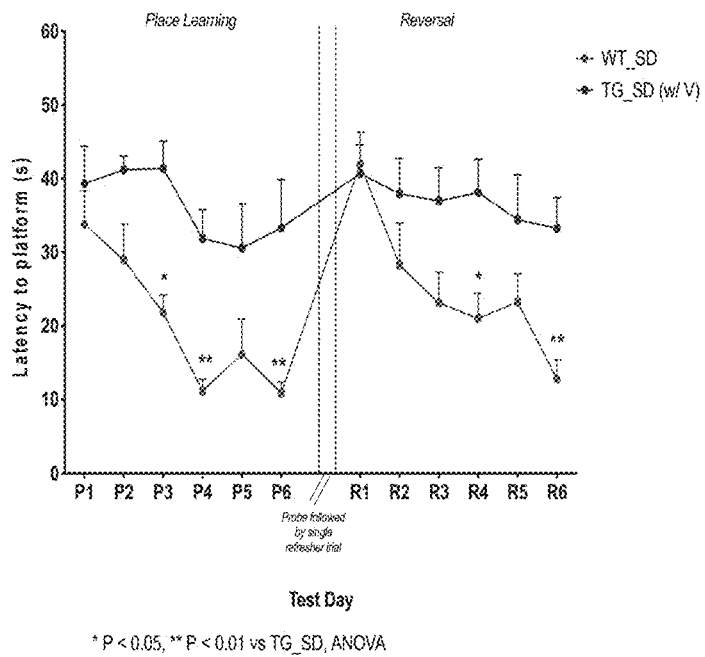
FIG. 11A. Latency during the hidden (submerged) platform place learning and reversal tasks. Data are mean±SEM. P: training days 1-6, R (reversed quadrant): training days 1-6. SD, standard diet; TG, transgenic; V, vehicle; WT, wild-type.
Figure 11B:
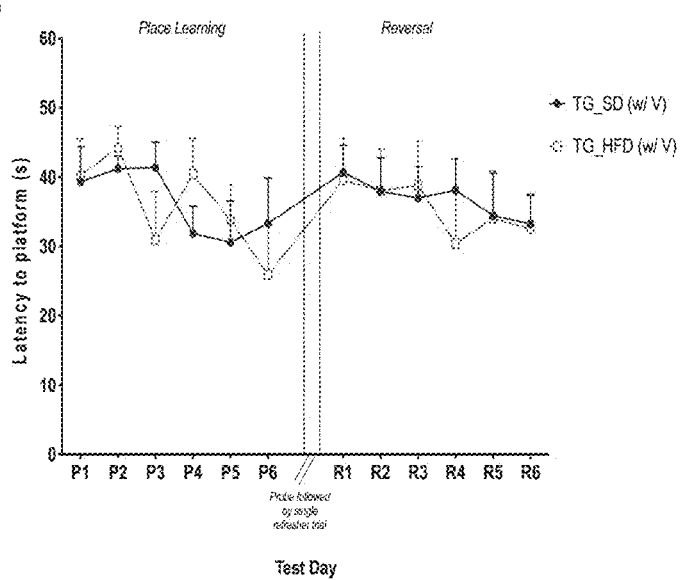
FIG. 11B. Latency during the hidden (submerged) platform place learning and reversal tasks. Data are mean±SEM. P: training days 1-6, R (reversed quadrant): training days 1-6. HFD, high fat diet; SD, standard diet; TG, transgenic; V, vehicle.
Figure 11C:
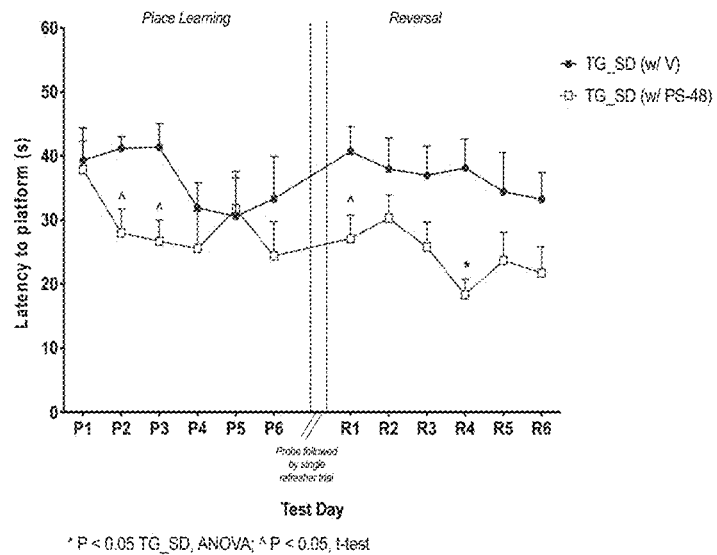
FIG. 11C. Latency during the hidden (submerged) platform place learning and reversal tasks. Data are mean±SEM. P: training days 1-6, R (reversed quadrant): training days 1-6. SD, standard diet; TG, transgenic; V, vehicle.
Figure 11D:
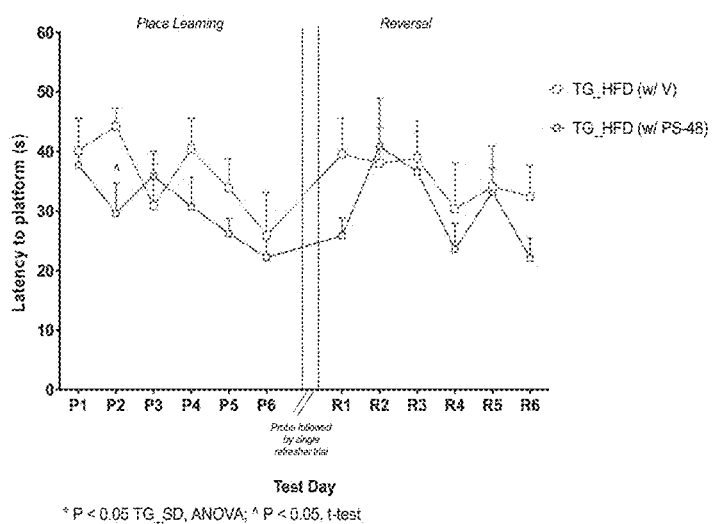
FIG. 11D. Latency during the hidden (submerged) platform place learning and reversal tasks. Data are mean±SEM. P: training days 1-6, R (reversed quadrant): training days 1-6. HFD, high fat diet; TG, transgenic; V, vehicle.

Next, a series of experiments was performed using a Morris water maze. WT mice fed standard diet (SD) reached the hidden platform in a shorter time compared to TG-SD mice. See FIG. 11A. In TG mice, high fat diet (HFD) did not significantly affect the latency to the hidden platform. See FIG. 11B. In APP/PS-1 TG mice, PS48 given orally through diet tended to reduce latency to reach the hidden platform within both SD (FIG. 11C) and HFD (FIG. 11D) conditions. The PS48 effect was more pronounced within the standard diet condition. *p<0.05, **p<0.01, ANOVA; ^p<0.05, t-test.

Figure 12A:
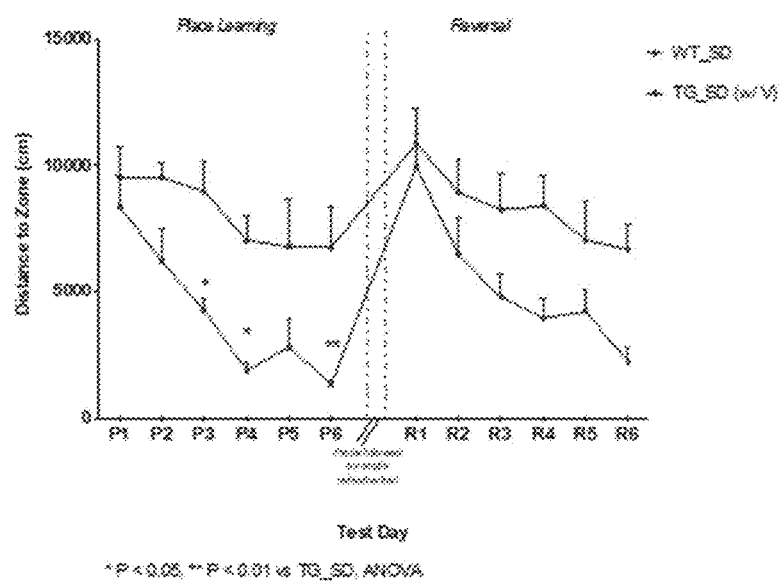
FIG. 12A. Distance to the zone during hidden platform place learning and reversal tasks. Data are mean±SEM. *$p<0.05$, **$p<0.01$, ANOVA. SD, standard diet; TG, transgenic; V, vehicle; WT, wild-type.
Figure 12B:
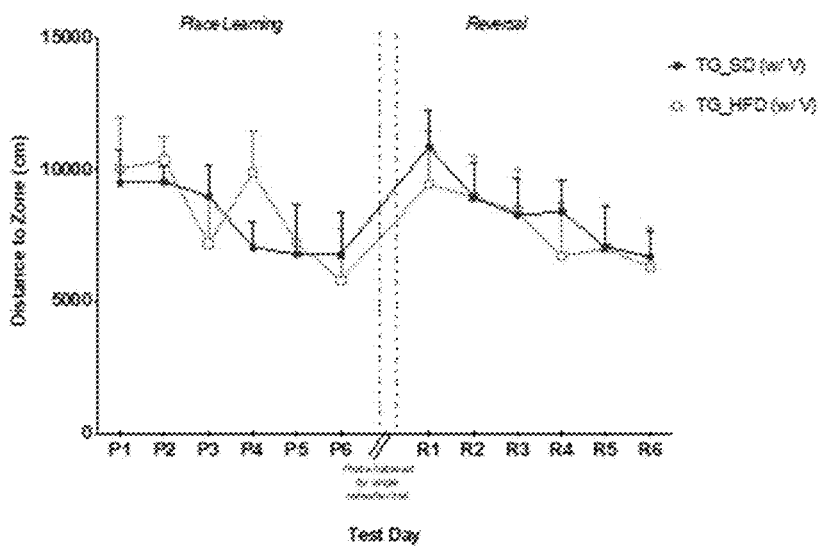
FIG. 12B. Distance to the zone during hidden platform place learning and reversal tasks. Data are mean±SEM. HFD, high fat diet; SD, standard diet; TG, transgenic; V, vehicle.
Figure 12C:
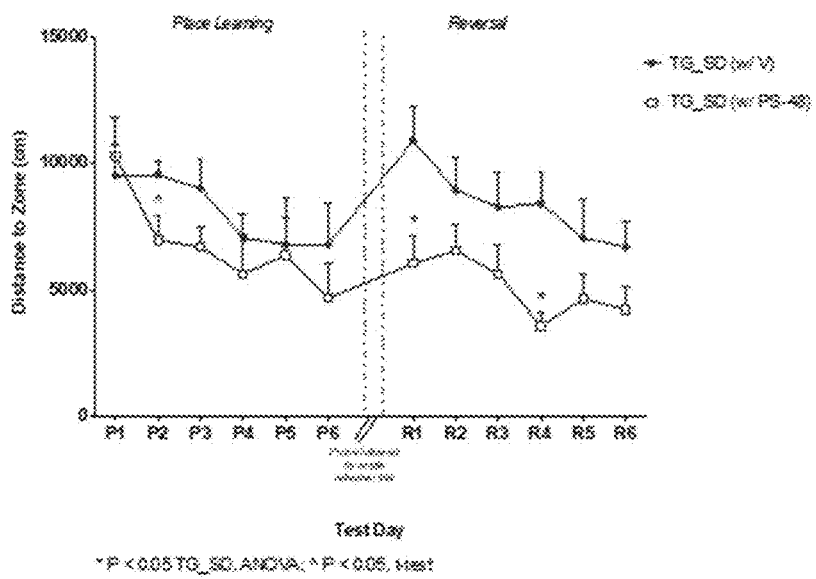
FIG. 12C. Distance to the zone during hidden platform place learning and reversal tasks. Data are mean±SEM. *$p<0.05$, ANOVA; ^$p<0.05$, t-test. SD, standard diet; TG, transgenic; V, vehicle.
Figure 12D:
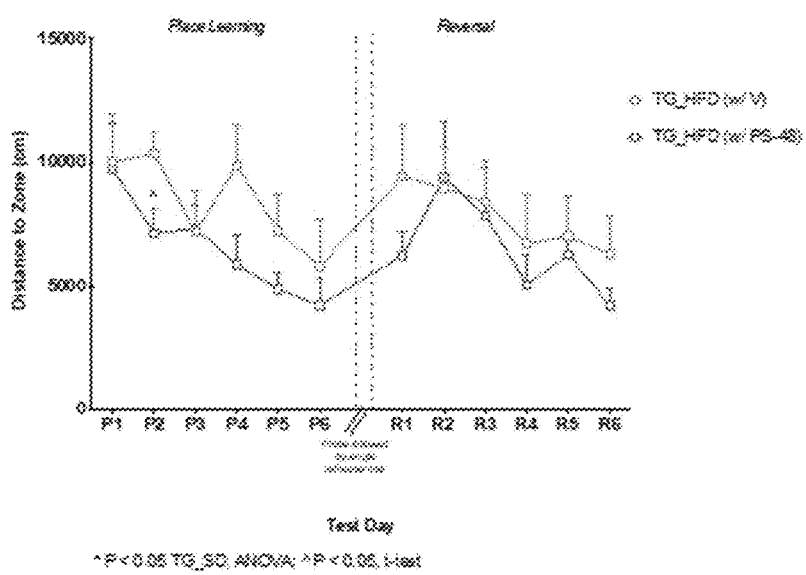
FIG. 12D. Distance to the zone during hidden platform place learning and reversal tasks. Data are mean±SEM. ^$p<0.05$, t-test. HFD, high fat diet; TG, transgenic; V, vehicle.

WT mice fed standard diet (SD) reached the hidden platform zone in a shorter distance compared to TG-SD mice. See FIG. 12A. In TG mice, high fat diet (HFD) did not significantly affect the distance to zone to the hidden platform vs standard diet (SD). See FIG. 12B. In APP/PS-1 TG mice, dietary PS48 tended to reduce distance to zone to reach the hidden platform within both SD (FIG. 12C) and HFD (FIG. 12D) conditions. The PS48 effect was more pronounced within the standard diet condition.

Figure 13B:
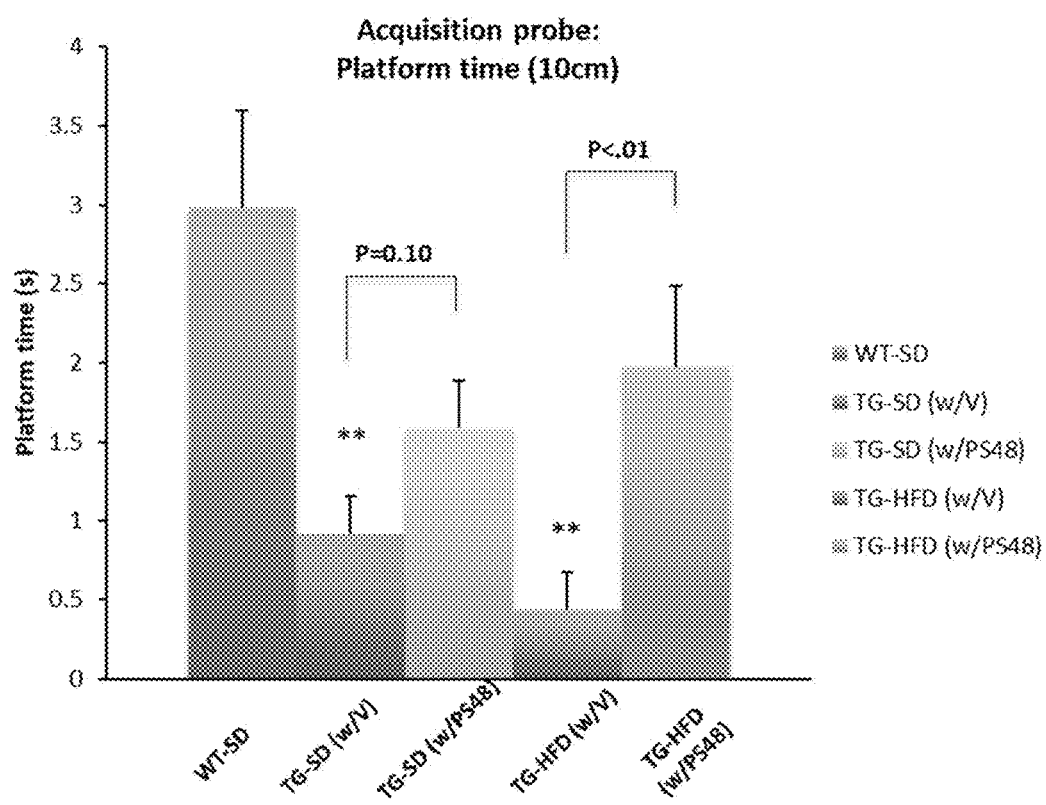
FIG. 13B. Time spent over the platform area in Morris Water Maze, acquisition probe. ** $p<0.01$ vs control (one-way ANOVA). p values on graph are independent t-tests. HFD, high fat diet; SD, standard diet; TG, transgenic; V, vehicle; WT, wild-type.

Memory acquisition for the location of the escape platform location was tested in 12-month-old APP/PS1 transgenic and littermate mice. The removed escape platform was located in the northeast quadrant of the tank. FIG. 13A shows track records of 2 representative animals from each group. The 10 cm platform is indicated in the figure by the shaded circle in the upper right quadrant. The following metrics were quantified: (1) time spent swimming over the target area, (2) latency to attain the target area, (3) path length to platform, and (4) number of crossings over the area. FIG. 13B shows time spent over the platform area. Wild type mice (control) averaged 3 seconds, indicating normal retention, whereas the AD 2x transgenic mice on standard diet swam for only a mean of 1 second over the platform area, indicating poor spatial recall. Animals fed standard diet with PS48 improved in this measure (p<0.10 vs vehicle fed). Transgenic animals fed high fat diet (HFD) performed less well than those on standard diet. When HFD was supplemented with PS48, they showed the most significant improvement (p<0.01 vs Tg HFD w/V).

Figure 13C:
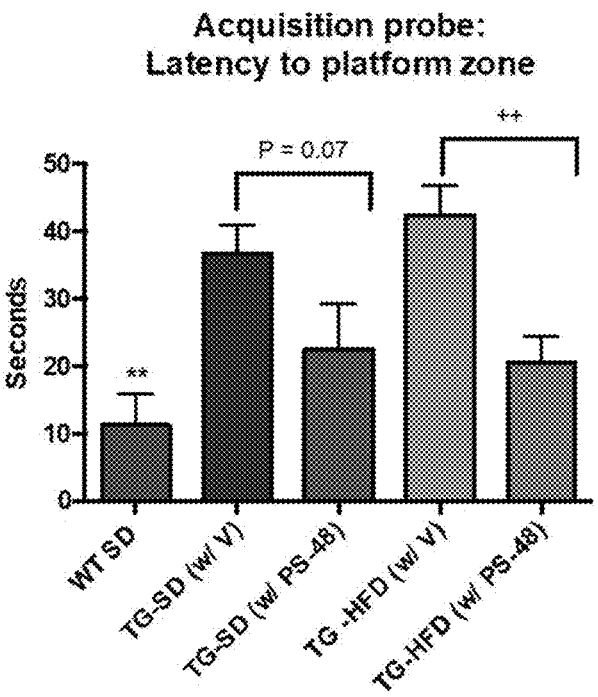
FIG. 13C. Latency to platform zone in Morris Water Maze, acquisition probe. HFD, high fat diet; SD, standard diet; TG, transgenic; V, vehicle; WT, wild-type. ** $p<0.01$ WT vs TG, standard diets; ++$p<0.01$ TG-HFD (with V) vs TG-HFD (with PS48).
Figure 13D:
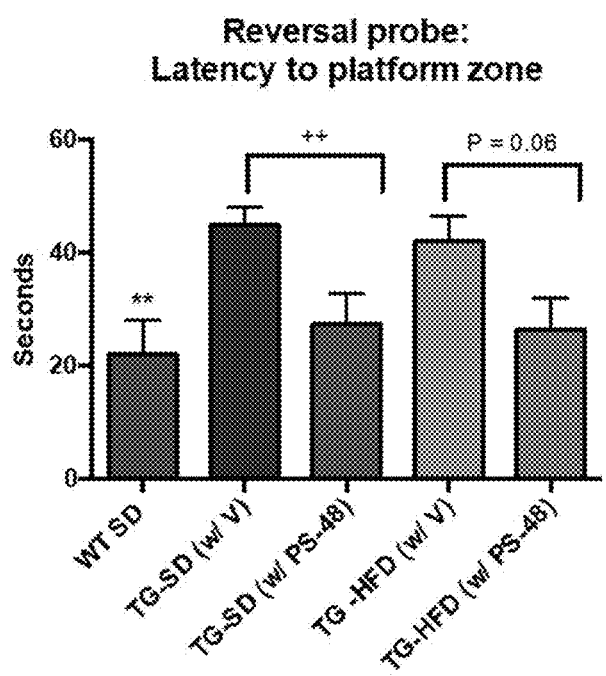
FIG. 13D. Latency to platform zone in Morris Water Maze, reversal probe. HFD, high fat diet; SD, standard diet; TG, transgenic; V, vehicle; WT, wild-type. ** $p<0.01$ WT vs TG, standard diets; ++$p<0.01$ TG SD (with V) vs TG SD (with PS48). Where comparisons did not reach statistical significance, p values are shown above.
Figure 13E:
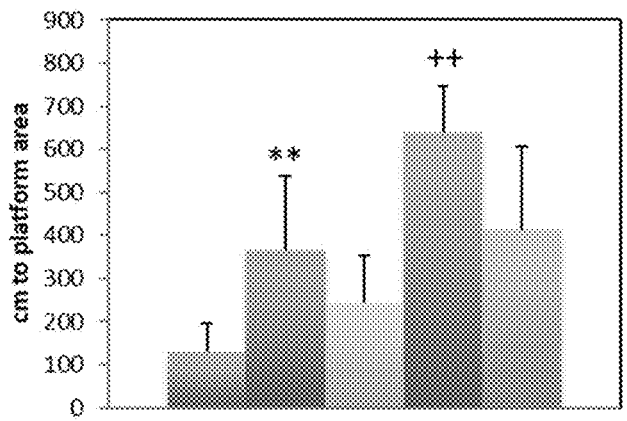
FIG. 13E. Path length to platform zone in Morris Water Maze, acquisition probe. See FIG. 13B for legend. Data are mean±SEM. HFD, high fat diet; SD, standard diet; TG, transgenic; V, vehicle; WT, wild-type. ** $p<0.005$, ++$p<0.001$. n=16 data points per group.
Figure 13F:
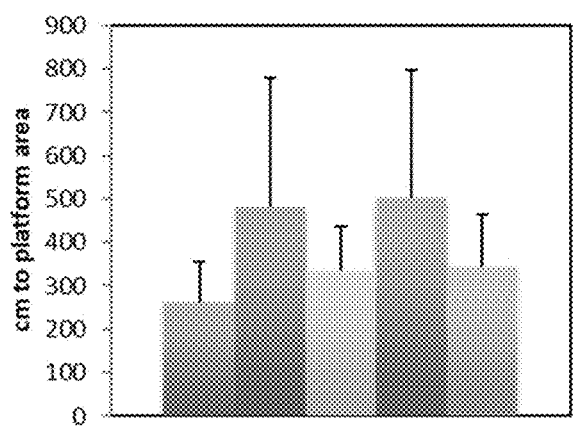
FIG. 13F. Path length to platform zone in Morris Water Maze, reversal probe. See FIG. 13B for legend. Data are mean±SEM. HFD, high fat diet; SD, standard diet; TG, transgenic; V, vehicle; WT, wild-type. * p<0.05, ** p<0.01. n=16 data points per group.
Figure 13G:
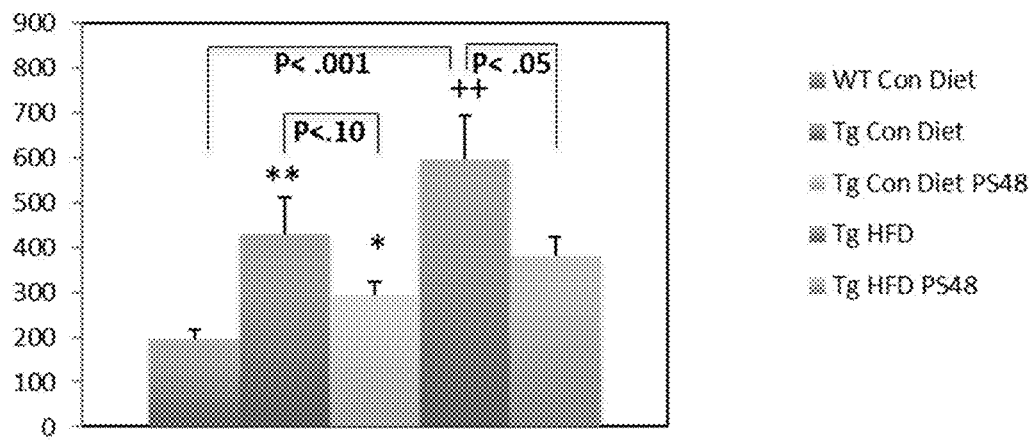
FIG. 13G. Path length to platform zone in Morris Water Maze, acquisition/reversal probe. Data are mean±SEM. Con Diet, control diet; HFD, high fat diet; Tg, transgenic; WT, wild-type. n=16 data points per group.
Figure 13H:
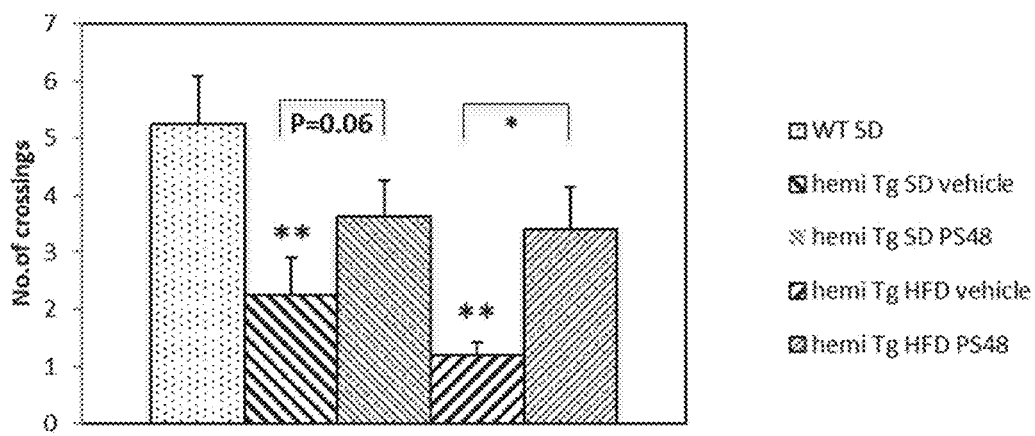
FIG. 13H. Crossing numbers over removed platform location in Morris Water Maze, acquisition/reversal probe. Data are mean±SEM. hemi, hemizygous; HFD, high fat diet; SD, standard diet; Tg, transgenic; WT, wild-type. * p<0.05, ** p<0.001.

FIG. 13C shows latency to platform, acquisition phase. The figure shows time in seconds taken to first reach platform area after release in the southeast (SE) quadrant. Similar findings were obtained between groups as in "time over target area" shown in FIG. 13B. Lower latency values indicate better recall for the target location. Results favored wild-type mice on standard diet and Tg mice treated with PS48 on either standard or high fat diet compared to their vehicle controls. FIG. 13D shows latency to platform in a reversal trial. Animals were retrained with the platform in the SE quadrant and probe phase conducted as before.

FIGS. 13E-13H show path length taken, in cm, to first reach hidden platform. Tg mice on standard and HFD diets took a significantly longer route compared to wild type. Animals in either group on PS48 trended improvements in the direction of WT. Similar probe results were obtained in the subsequent reversal trial. When both data are combined for the same animal, the Tg HFD group significantly benefited from dietary PS48. (±1 SEM, n=16 data points per group, * p<0.05, ** p<0.01, ++p<0.001).

FIG. 13I shows crossing numbers over removed platform location, directly counted from track records in FIG. 13A. The data has similar import to time spent over platform area above. Data from both probe trials were combined, n=12 records per group. ** p<0.001 vs WT, the Tg animals in both the standard/PS48 and HFD/PS48 group (bars 3 and 5) were not significantly different from WT. The Tg PS48 group performed significantly better than vehicle (* p<0.05).

Figure 14A:
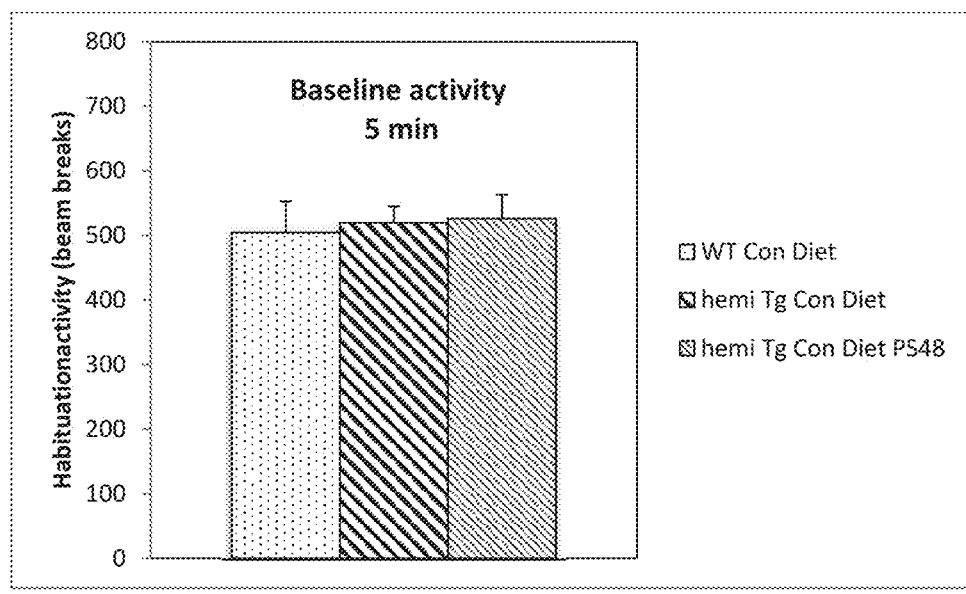
FIG. 14A. Contextual and cued fear conditioning. Baseline freezing on Day 1. Data are mean±SEM. Con Diet, control diet; hemi, hemizygous; Tg, transgenic; WT, wild-type.
Figure 14B:
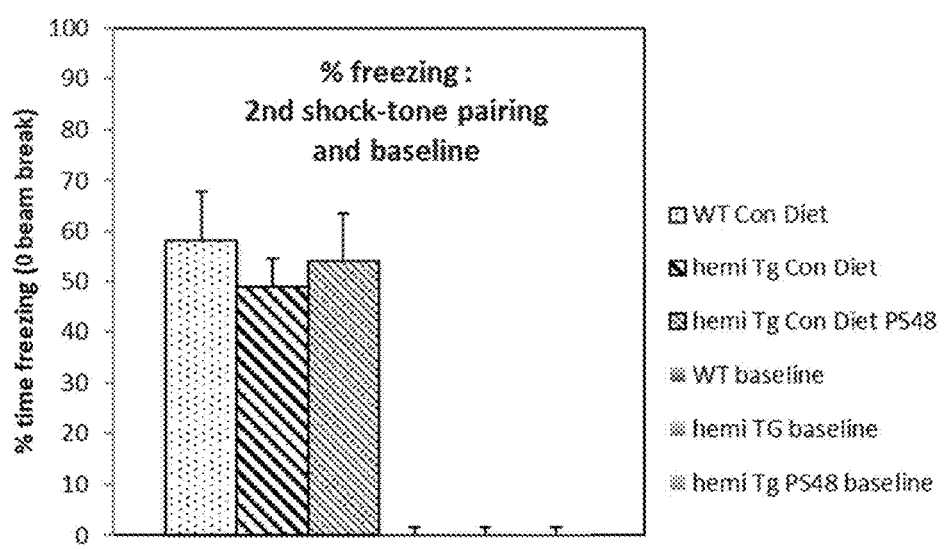
FIG. 14B. Freezing to shock. Data are mean±SEM. Con Diet, control diet; hemi, hemizygous; Tg, transgenic; WT, wild-type.

Next, a series of experiments was performed to assess contextual and cued fear conditioning. 16-month-old mice WT, TG w/vehicle, and TG w/PS48 were first habituated to establish activity levels (300 sec), then presented 3 shock-tone pairings, followed by probes of contextual and cued fear memory. Prior to conditioning to the tone and foot shock, mice in all groups experienced very low levels of freezing (Baseline Freezing Day 1) (FIG. 14A) and the expected freezing to the shock (FIG. 14B). Levels of freezing were markedly higher than baseline, indicating that all animals were able to learn and remember an association between the aversive foot shock (unconditioned stimulus (US)) and the neutral conditioned stimulus (CS, in this case the context).

Figure 14C:
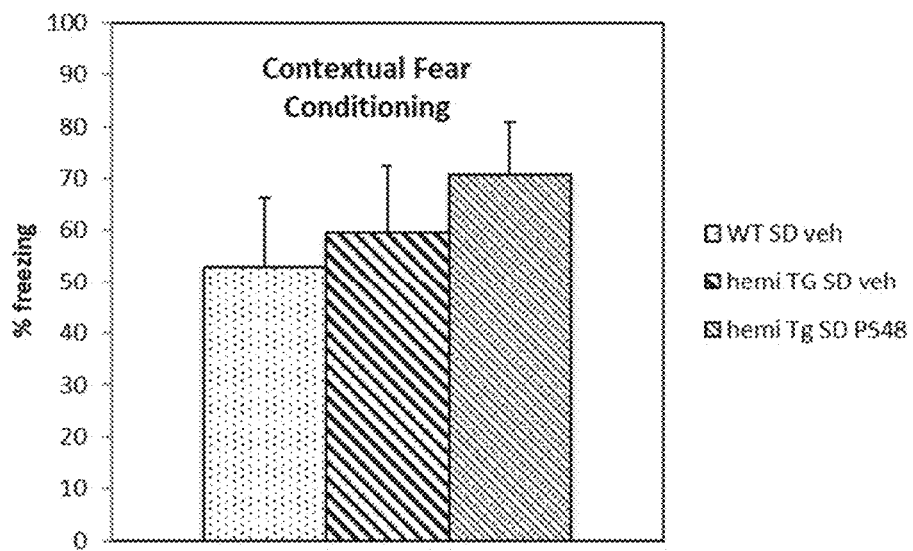
FIG. 14C. Contextual fear conditioning. Data are mean±SEM. hemi, hemizygous; SD, standard diet; TG or Tg, transgenic; veh, vehicle; WT, wild-type.

After the conditioning procedure, when mice were placed back in the same context but without tone or shock (Day 2), freezing was measured over 8 minutes, the last 4 minutes were quantified. See FIG. 14C.

Figure 14D:
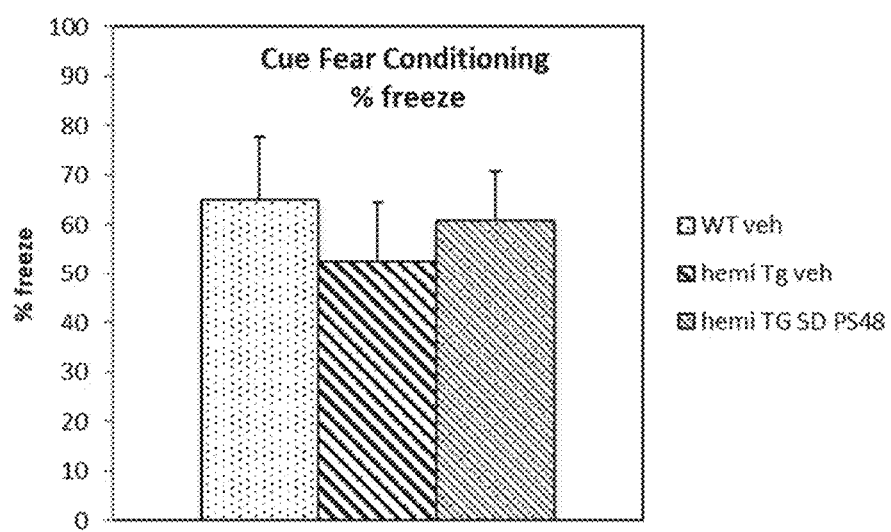
FIG. 14D. Cue fear conditioning. Data are mean±SEM. hemi, hemizygous; SD, standard diet; TG or Tg, transgenic; veh, vehicle; WT, wild-type.

On Day 3 the context was changed for 2 minutes (12 bins) and mice were exposed to a continuous tone (cue) used during conditioning for 8 minutes. Mice generally had a low level of Baseline Freezing Day 3 in the altered context before being exposed to the tone, with markedly higher general freezing upon re-exposure to the tone, indicating that all animals were able to learn and remember an association between the aversive foot shock unconditioned stimulus (US) and the neutral cue conditioned stimulus (CS, in this case the tone). Freezing % was quantified as the number of 10-sec epochs in which there was no beam break over the total number of epochs in the 4-minute period (24). While no significant changes were noted, a trend in cue conditioning paradigm favored PS48 treatment in Tg mice. See FIG. 14D.

Finally, a series of in vivo experiments was performed to assess safety of treatment with PS48. Preliminary data in normal mice did not evidence overt drug toxicity or alteration in glucose metabolism when PS48 was given intravenously (IV) over 2 weeks. Similarly, when PS48 was given by oral gavage over 2 weeks, there were no signs of toxicity by gross observation, organ specific necropsy, or weight.

Figure 15A:
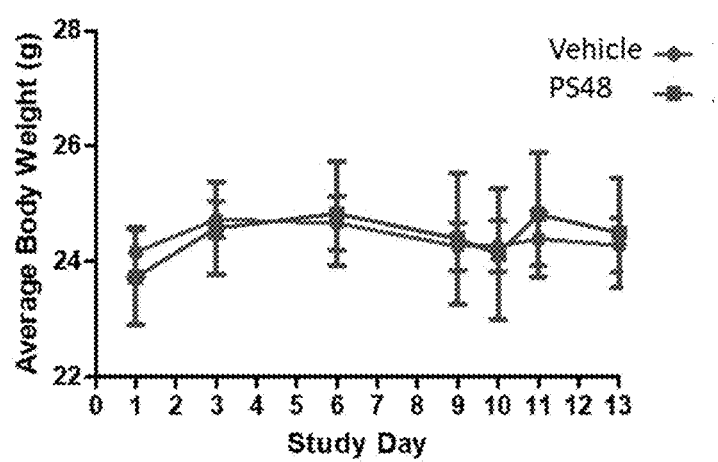
FIG. 15A. Average body weight on daily PS48 or vehicle administered intravenously. n=6 for each group.
Figure 16:
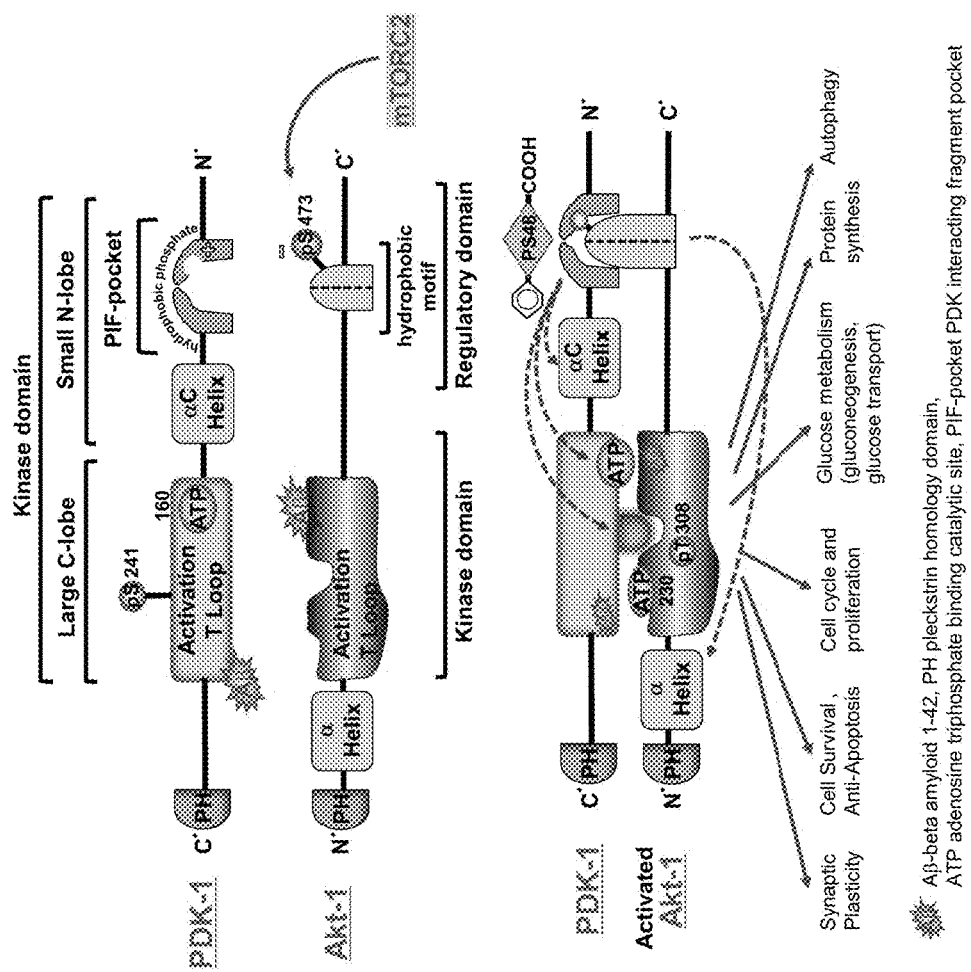
FIG. 16. Schematic of allosteric modulation of PDK-1 and activation of Akt in the presence of Aβ42. Allosteric modulators of PDK-1 such as PS48, target the PDK-interacting fragment (PIF) pocket, which is also the docking site for the AGC class kinase substrates of PDK-1 (Akt, p70S6k, SGK, PKC/PRK-2). The model shows the steric inhibitory effect of A342 on insulin-stimulated Akt activation by PDK-1 (upper panel) and allosteric modulation by PS48 to overcome it (lower panel).

For intravenous PS48, adult male C57BL/6 mice (Charles River, n=6 per group) were fed ad libitum and dosed with PS48 or vehicle in an escalating schedule from 3-20 mg/kg IV daily; 3-10 mg/kg days 1-6, and 20 mg/kg days 7-13. Tail vein blood sugars were obtained 30, 60, and 120 minutes after every third dose. No behavioral changes were evident during the 2-week trial. Gross necropsy after 14 days revealed no abnormalities. There was no significant change in mean body weight or mean blood sugars (mg/dl). See FIG. 15A.

Liver transaminases ALT and AST, as well as muscle creatine kinase (CK), were also measured to assess possible liver toxicity and possible general tissue toxicity, respectively. A change in ALT, albeit statistically significant, was very small. See FIG. 15B. There was no significant change in CK with PS48. See FIG. 15C.

PS48 administered by oral gavage was also well tolerated. Adult C57BL/6 mice (n=6 per group) were administered PS48 for 14 days. A low dose group received 1 mg/kg per day, while a high dose group received 50 mg/kg per day. A negative control group received corn oil.

No overt behavioral changes were noted. Body and organ specific weights were unaffected at necropsy. See FIG. 15D. Fasting serum glucose at trial end was unchanged (~150 mg/dl). See FIG. 15E.

INCORPORATION BY REFERENCE

All of the scientific and patent publications referred to herein are incorporated herein by reference in their entirety. In the event of conflicting disclosures, the present detailed description is controlling.

Those skilled in the art will recognize, or be able to ascertain using no more than routine experimentation, many equivalents to the specific embodiments of the invention described herein. Such equivalents are intended to be encompassed by the following claims.

I claim:

1. A method of improving learning and memory, comprising administering to a subject in need thereof an effective amount of a compound selected from the group consisting of:

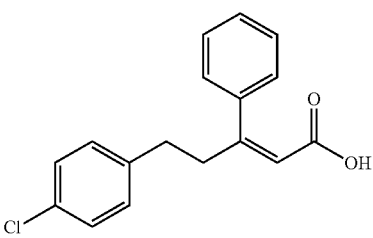 [SMILES: O=C(O)/C=C(/CCc1ccc(Cl)cc1)c1ccccc1]

((Z)-5-(4-chlorophenyl)-3-phenylpent-2-enoic acid; PS48);

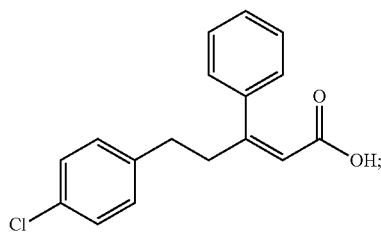

((Z)-5-(4-chlorophenyl)-3-phenylpent-2-enoic acid; PS48)

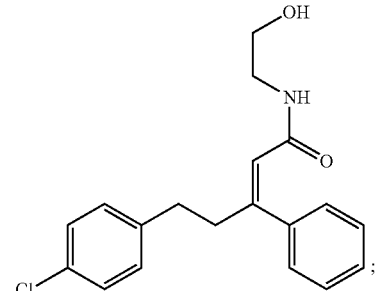

((Z)-5-(4-chlorophenyl)-N-(2-hydroxyethyl)-3-phenylpent-2-enamide; 508-1-7)

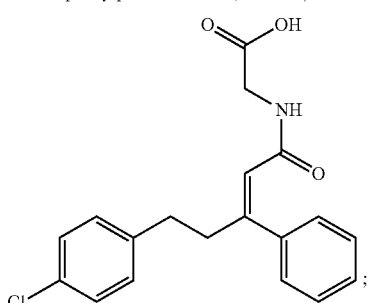

((Z)-5-(4-chlorophenyl)-3-phenylpent-2-enoyl)glycine; 508-1-25)

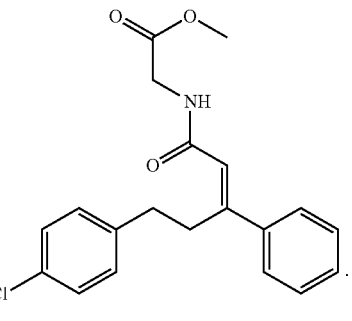

(1-(4-(trifluoromethoxy)benzyl)-1H-indole-3-carboxylic acid; 508-1-31)

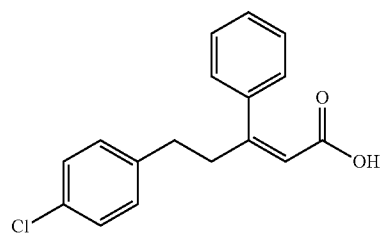 [SMILES: O=C(O)/C=C(/CCc1ccc(Cl)cc1)c1ccccc1]

(methyl (Z)-(5-(4-chlorophenyl)-3-phenylpent-2-enoyl)glycinate; 508-1-68)

2. The method of claim 1, wherein the subject has Alzheimer's Disease.

3. The method of claim 1, wherein
the effective amount is about 1 mg/kg/day to about 50 mg/kg/day.

4. The method of claim 1, wherein the administering is orally administering.

5. The method of claim 1, wherein the effective amount is at least about 10 mg/kg/day.

6. The method of claim 1, wherein the administering is parenterally administering.

7. The method of claim 1, wherein the compound is

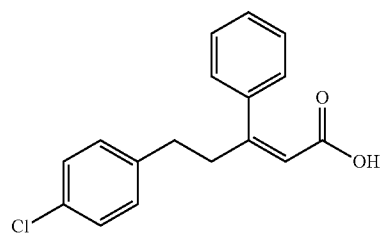 [SMILES: O=C(O)/C=C(/CCc1ccc(Cl)cc1)c1ccccc1]

((Z)-5-(4-chlorophenyl)-3-phenylpent-2-enoic acid; PS48).

8. The method of claim 1, wherein the compound is

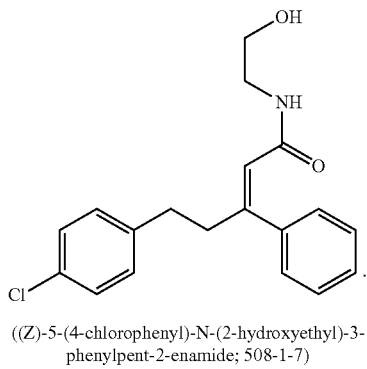 [SMILES: O=C(/C=C(/CCc1ccc(Cl)cc1)c1ccccc1)NCCO]

((Z)-5-(4-chlorophenyl)-N-(2-hydroxyethyl)-3-phenylpent-2-enamide; 508-1-7)

9. The method of claim 1, wherein the compound is

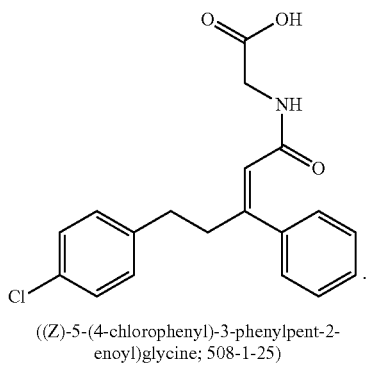 [SMILES: O=C(O)CNC(=O)/C=C(/CCc1ccc(Cl)cc1)c1ccccc1]

((Z)-5-(4-chlorophenyl)-3-phenylpent-2-enoyl)glycine; 508-1-25)

10. The method of claim 1, wherein the compound is

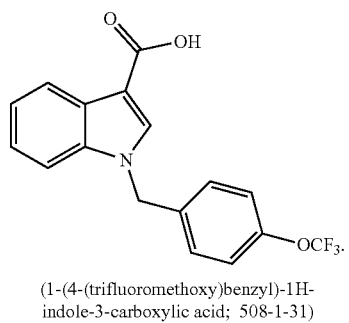 [SMILES: O=C(O)c1cn(Cc2ccc(OC(F)(F)F)cc2)c2ccccc12]

(1-(4-(trifluoromethoxy)benzyl)-1H-indole-3-carboxylic acid; 508-1-31)

11. The method of claim 1, wherein the compound is

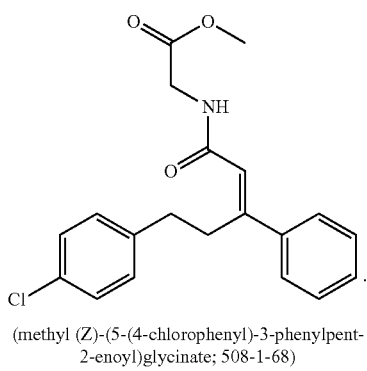 [SMILES: COC(=O)CNC(=O)/C=C(\CCc1ccc(Cl)cc1)c1ccccc1]

(methyl (Z)-(5-(4-chlorophenyl)-3-phenylpent-2-enoyl)glycinate; 508-1-68)

\* \* \* \* \*